(12) United States Patent
Parker et al.

(10) Patent No.: US 8,501,398 B2
(45) Date of Patent: Aug. 6, 2013

(54) LUMINESCENCE ASSAY USING MACROCYCLIC LANTHANIDE (III) COMPLEXES

(75) Inventors: David Parker, Durham City (GB); Robert Anthony Poole, Durham (GB); Filip Kielar, Durham (GB)

(73) Assignee: University of Durham, Durham (GB)

( * ) Notice: Subject to any disclaimer, the term of this patent is extended or adjusted under 35 U.S.C. 154(b) by 387 days.

(21) Appl. No.: 12/373,075

(22) PCT Filed: Jul. 11, 2007

(86) PCT No.: PCT/GB2007/002592
§ 371 (c)(1), (2), (4) Date: Oct. 15, 2009

(87) PCT Pub. No.: WO2008/007089
PCT Pub. Date: Jan. 17, 2008

(65) Prior Publication Data
US 2010/0055665 A1 Mar. 4, 2010

(51) Int. Cl.
*C12Q 1/00* (2006.01)
*G01N 33/00* (2006.01)

(52) U.S. Cl.
USPC .............................. 435/4; 435/968; 436/131

(58) Field of Classification Search
None
See application file for complete search history.

(56) References Cited

U.S. PATENT DOCUMENTS

| | | | |
|---|---|---|---|
| 6,563,585 B1 | 5/2003 | Rao et al. | |
| 6,750,005 B2 * | 6/2004 | Leif et al. | 435/4 |
| 7,517,701 B2 * | 4/2009 | Parker et al. | 436/546 |
| 2008/0312431 A1 * | 12/2008 | Parker et al. | 540/474 |

FOREIGN PATENT DOCUMENTS

| WO | WO 99/46600 | 9/1999 | |
|---|---|---|---|
| WO | WO 00/42048 A | 7/2000 | |
| WO | WO 01/20334 | 3/2001 | |
| WO | WO 03/035655 | 5/2003 | |
| WO | WO 2005/046735 | 5/2005 | |
| WO | WO 2006/039505 | 4/2006 | |
| WO | WO/2006/039505 | * | 4/2006 |

OTHER PUBLICATIONS

Poole et al., "A ratiometric and non-enzymatic luminescence assay for uric acid: differential quenching of lanthanide excited states by anti-oxidants," Chem. Commun., 2006, issue 39, pp. 4084-4086.*
Horiguchi, et al., "A Novel Time-Resolved Fluoroimmunoassay Using a Macrocyclic Europium Ligand as a Label," Chem. Pharm. Bull., 42(4), 972-975 (1994).
Poole et al., "Synthesis and characterisation of highly emissive and kinetically stable lanthanide complexes . . . in cellulo," Org. Biomol. Chem., 3, 1013-1024 (2005).
Atkinson, et al., "Azaxanthones and azathioxanthones are effective sensitizers for europium and terbium luminescence," Org. Biol. Chem., 4, 1707-1722 (2006).
Quici, et al., "Highly Luminescent Eu3+ and TB3+ Macrocyclic Complexes Bearing an Appended Phenanthroline Chromophore," Inorganic Chem., 41, 2777-2784 (2002).
Simic, et al., "Antioxidation Mechanisms of Uric Acid," J. Am. Chem. Soc. 111, 5778-5782 (1989).
Steenken, et al., "One-Electron Redox Potentials of Phenos, Hydroxy- and Aminophenols and Related Compounds of Biological Interest," J. Phys. Chem., 86, 3861-3867 (1982).

* cited by examiner

Primary Examiner — Shafiqul Haq
Assistant Examiner — Galina Yakovleva
(74) Attorney, Agent, or Firm — Berenato & White, LLC.

(57) ABSTRACT

The invention provides a method of determining the amount of an analyte having an oxidation potential, for a one electron oxidation process, of about +0.10 to about +1.20 volts at pH 7, relative to the normal hydrogen electrode at 298K, said method comprising measuring the emission intensity or emission lifetime, at two or more wavelengths, from a sample comprising said analyte and two or more different macrocyclic lanthanide (III) complexes, wherein each of said macrocyclic lanthanide (III) complexes comprises a different lanthanide ion but the same macrocyclic ligand, and using a ratio of emission intensities or emission lifetimes measured at two different wavelengths to calculate the amount of analyte in said sample.

28 Claims, 8 Drawing Sheets

LUMINESCENCE ASSAY USING MACROCYCLIC LANTHANIDE (III) COMPLEXES

This application is a national stage application under 35 USC 371 of PCT/GB2007/002592, filed Jul. 11, 2007.

This invention provides a method of determining the amount of an analyte in a sample of, typically, a biological fluid by conducting a ratiometric luminescence assay employing two or more macrocyclic lanthanide (III) complexes; a mixture of two or more macrocyclic lanthanide (III) complexes which may be used in such a method; and a kit of parts comprising two or more such macrocyclic lanthanide (III) complexes.

INTRODUCTION

In humans, uric acid ($pK_a$ 5.7, MW 168) is the final breakdown product of purine (e.g. adenine, guanine) metabolism. Purines from nucleic acid breakdown are converted to uric acid in the liver. The uric acid is transported to the kidney where it is filtered by the glomerulus; 98% is reabsorbed by the proximal tubules and secreted by the distal tubules, ultimately appearing in the urine. The body uric acid level is determined by the balance between synthesis and urinary elimination. Hyperuricaemia is divided into primary and secondary forms, involving either over-production or reduced elimination. Primary hyperuricaemia is usually due to reduced tubular secretion of urate and in 1% of these patients this condition is linked to an enzymatic defect in purine metabolism. These patients lack phosphoribosyl transferase, leading to Lesch-Nyhan syndrome, a sex-linked genetic disorder.

Elevated levels of uric acid (hyperuricaemia) are most commonly associated with gout, increased breakdown of cell nuclei and renal disease. Patients on chemotherapy for proliferative diseases such as lymphoma, leukaemia or myeloma often exhibit hyperuricaemia and levels must be monitored to avoid kidney damage. Treatment involves administration of allopurinol, an inhibitor of uric acid synthesis. In gout patients, precipitation of uric acid in the joints leads to pain and inflammation and in many examples, this is directly linked to over-production of uric acid. Plasma uric acid levels in such patients are usually high (above 60 mgs per liter [0.36 mmol] cf. 1.5 to 4.5 mmol/liter in urine). Patients with gout are also susceptible to the formation of kidney stones (renal calculi).

Secondary hyperuricaemia may be caused by increased ingestion of foods rich in purines (shellfish/liver/kidney), leading to increased uric acid excretion. Secondary hyperuricaemia is linked to many conditions including excess alcohol consumption, haemolytic diseases, renal insufficiency, starvation/fasting, myeloproliferative diseases and lead intoxication. Hypouricaemia is much less common but may occur from under-production of uric acid, as in hereditary xanthinuria, toxemia in pregnancy, hereditary purine nucleoside phosphorylase deficiency and allopurinol therapy. Hypouricaemia (as measured u in a urine analysis) may also result from a reduction in uric acid excretion, as may occur in AIDS, diabetes mellitus and various malignant diseases.

Measurement of uric acid excretion may assist in the treatment regime for hyperuricaemia, involving either use of uricosuric drugs, to enhance renal excretion or allopurinol to suppress purine synthesis.

Current in vitro clinical assays used to measure uric acid in urine and serum are predominantly based on the use of the uricase enzyme, which catalyses the hydrolysis of uric acid leading to formation of the more water-soluble compound, allantoin, and hydrogen peroxide. The hydrogen peroxide is detected either directly via oxidation of a phenolic dye to produce a strongly coloured compound, or indirectly by the action of a peroxidase enzyme, leading to formation of an intensely coloured chromogen or a strongly emissive fluorophore. These enzymatic methods are typically subject to interference from ascorbate (requiring co-administration of ascorbate oxidase) and bilirubin. Typically, clinical kits give a linear response for the range 0.09 to 1.8 mmol/liter for serum and plasma, and 0.12 to 6 mmol/liter for urine. Detection limits fall in the 5 µmol/liter range for serum analysis and 40 µmol/liter for urine. The analysis requires incubation for at least 30 minutes, careful control of the pH of the analyses, the enzymes must be stored carefully to avoid protein denaturation, and the organic dyes used are often light and temperature sensitive, requiring storage in the dark at low temperatures.

SUMMARY OF THE INVENTION

We have surprisingly found that macrocyclic lanthanide (III) complexes such as those described herein may be used directly in assaying the amounts, or concentrations, of analytes of interest found in biological fluids, i.e. fluids such as urine or sera obtainable from living systems, particularly mammals and more particularly humans.

Lanthanide ions afford considerable scope for the development of new chemical entities that can be used as analytical or imaging probes, as components of optoelectronic devices, or as key sensor materials. Particular advantages of f-block ions are their intense, line-like and long-lived luminescence at a range of wavelengths spanning the visible and near infrared (NIR) regions, which permits time-gated rejection of unwanted signals arising from (short-lived) auto-fluorescence from biomolecules. This invention arises from the use of two or more different macrocyclic lanthanide (III) complexes, in which the complexes differ in the lanthanide ion co-ordinated by a common macrocyclic ligand, to assay for analytes, such as uric acid, of biological interest.

Viewed from a first aspect, therefore, the invention provide a method of determining the amount of an analyte having an oxidation potential, for a one electron oxidation process, of about +0.10 to about +1.20 volts, at pH 7, relative to the normal hydrogen electrode at 298K, said method comprising measuring the emission intensity or emission lifetime, at two or more wavelengths, from a sample comprising said analyte and two or more different macrocyclic lanthanide (III) complexes, wherein each of said macrocyclic lanthanide (III) complexes comprises a different lanthanide ion but the same macrocyclic ligand, and using a ratio of emission intensities or emission lifetimes measured at two different wavelengths to calculate the amount of analyte in said sample.

Viewed from a further aspect, the invention provides a mixture of two or more macrocyclic lanthanide (III) complexes according to the first aspect of the invention, each of which comprises a different lanthanide ion but comprises the same macrocyclic ligand.

Viewed from a still further aspect the invention provides a kit of parts comprising two or more macrocyclic lanthanide (III) complexes according to the first aspect of the invention, each of which comprises a different lanthanide ion but comprises the same macrocyclic ligand.

DETAILED DESCRIPTION OF THE INVENTION

Figure 1:
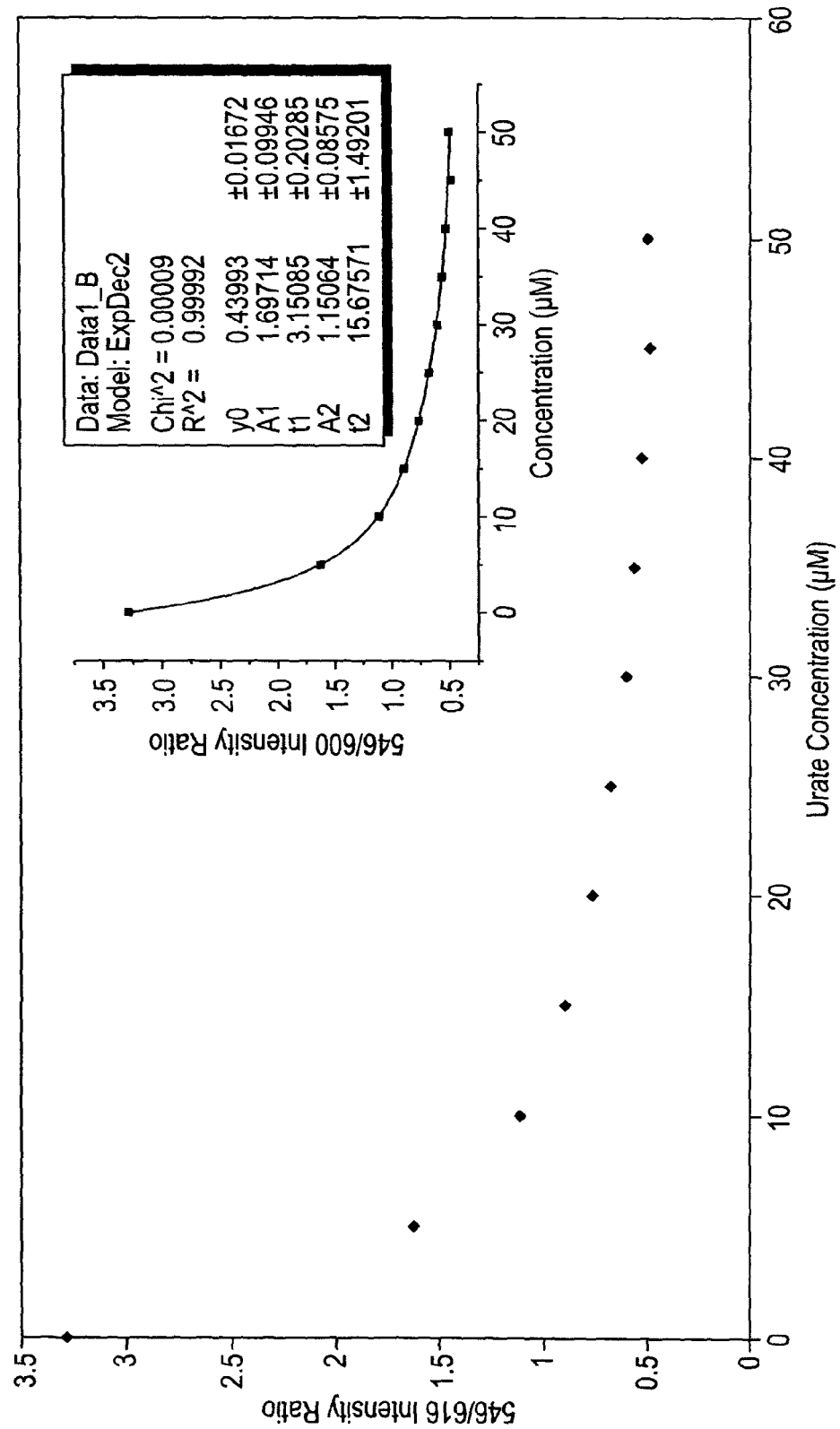
FIG. 1 shows the variation of the emission intensity of the 546 nm terbium emission band/616 nm europium band as a function of added urate concentration (pH 7.4, 298K, 0.1 M phosphate buffer).
Figure 2:
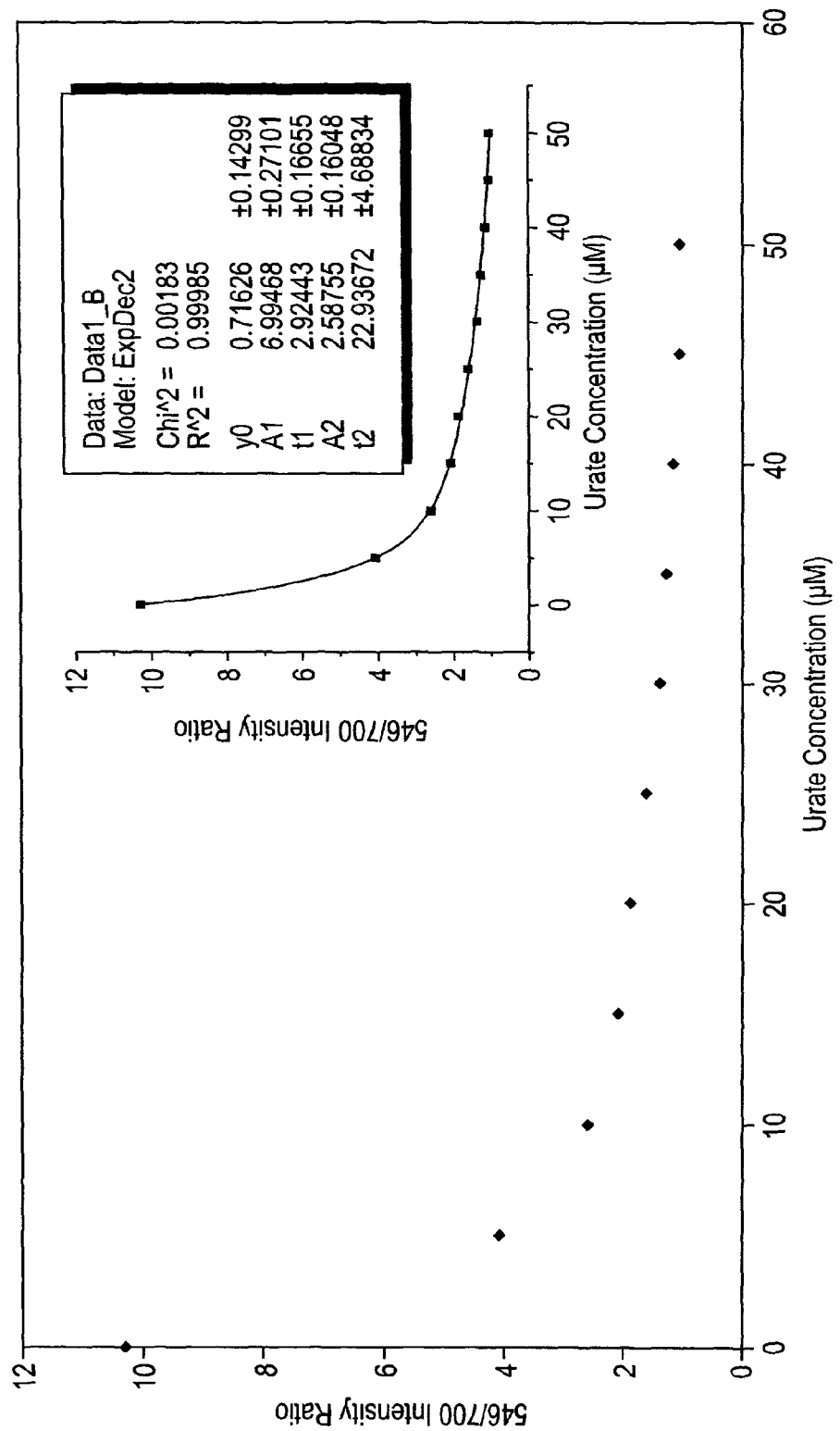
FIG. 2 shows the variation of the emission intensity of the 546 nm terbium emission band/700 nm europium band as a function of added urate concentration (pH 7.4, 298K, 0.1 M phosphate buffer).
Figure 3A:
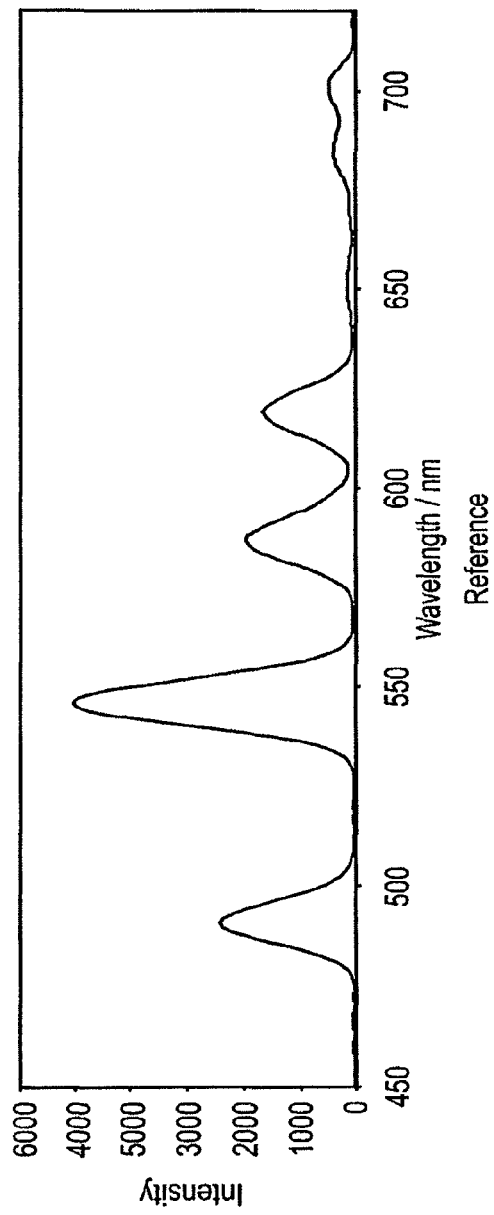
FIGS. 3A to 3F show the total emission spectra for a 1:1 mixture of [Eu.1] and Tb.1] wherein [Eu.1] and [Tb.1] are europium and terbium complexes of the macrocyclic ligand of formula 1 described herein, in which R=$CO_2^-$ and R'=$(CH_2)CO_2^-$, in the presence of increasing concentrations of sodium urate ($\lambda_{ex}$ 313 nm, pH 7.4, 298K). In each spectrum, the vertical axis is unitless since it refers to relative emission intensity.
Figure 3A:
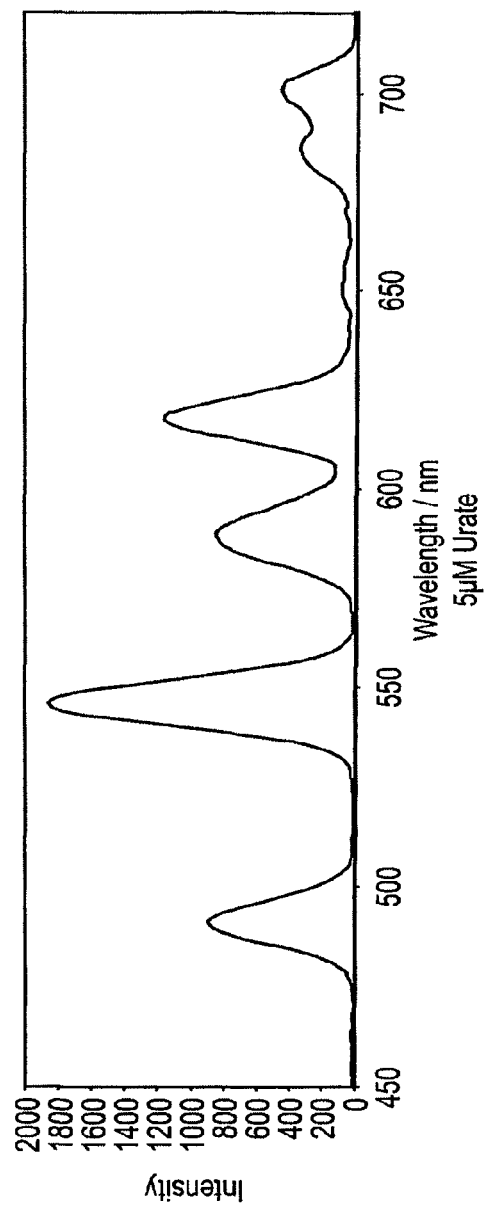
Figure 3B:
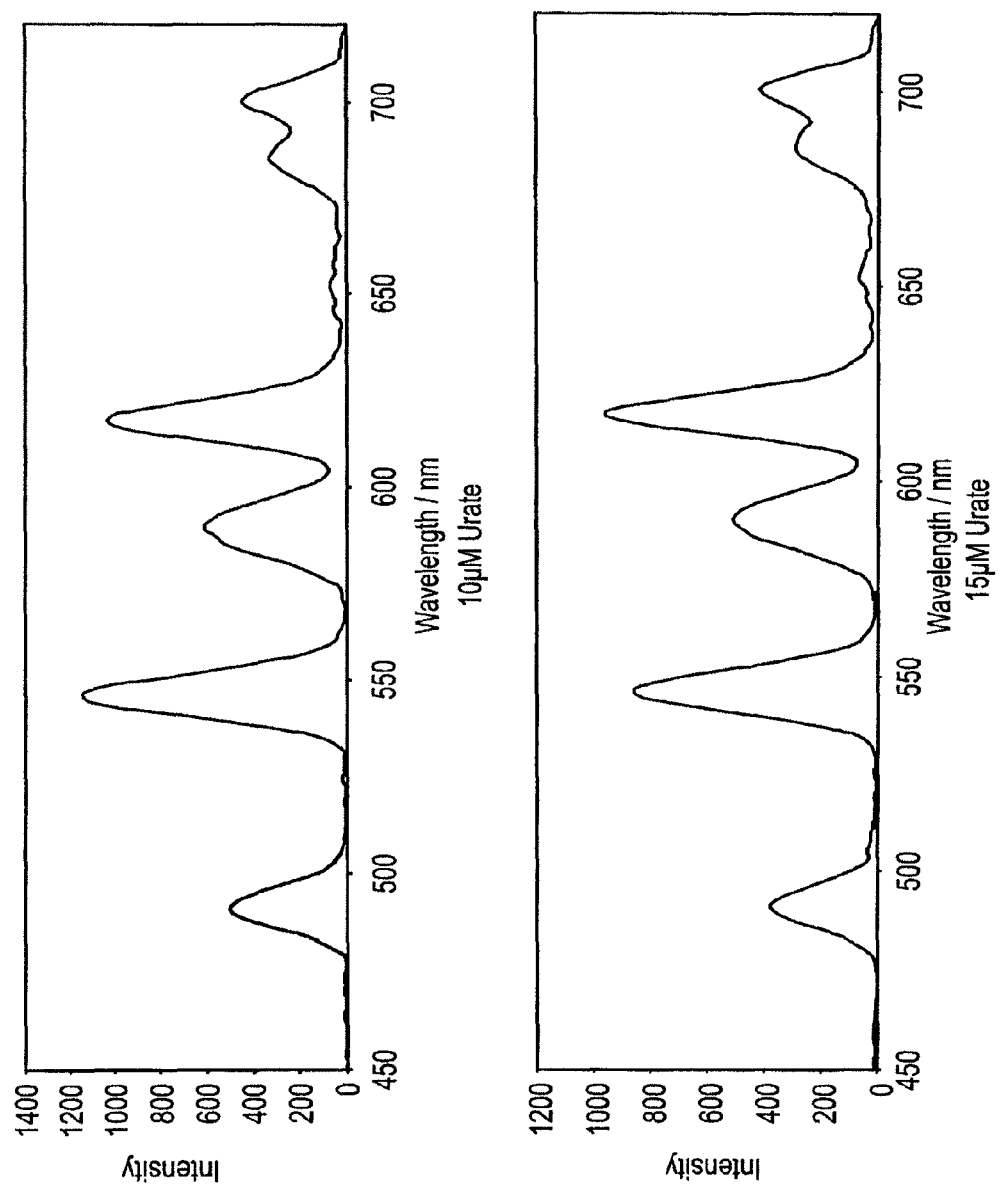
Figure 3C:
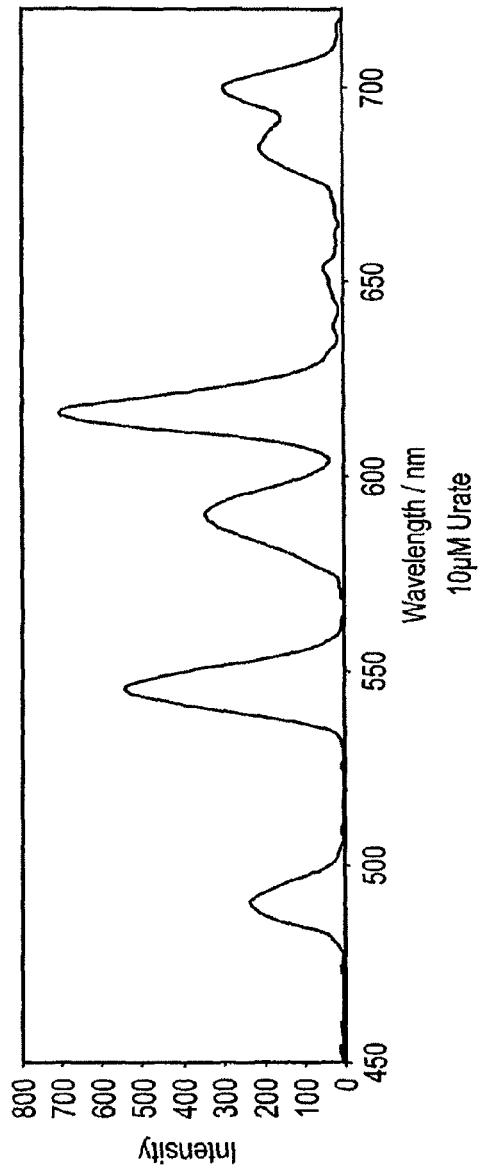
Figure 3C:
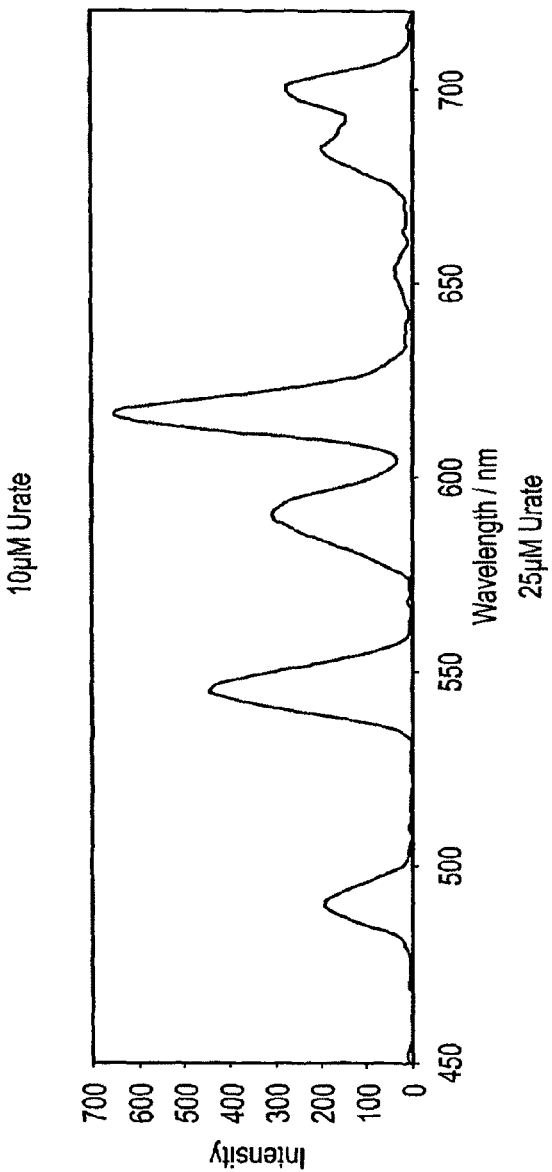
Figure 3D:
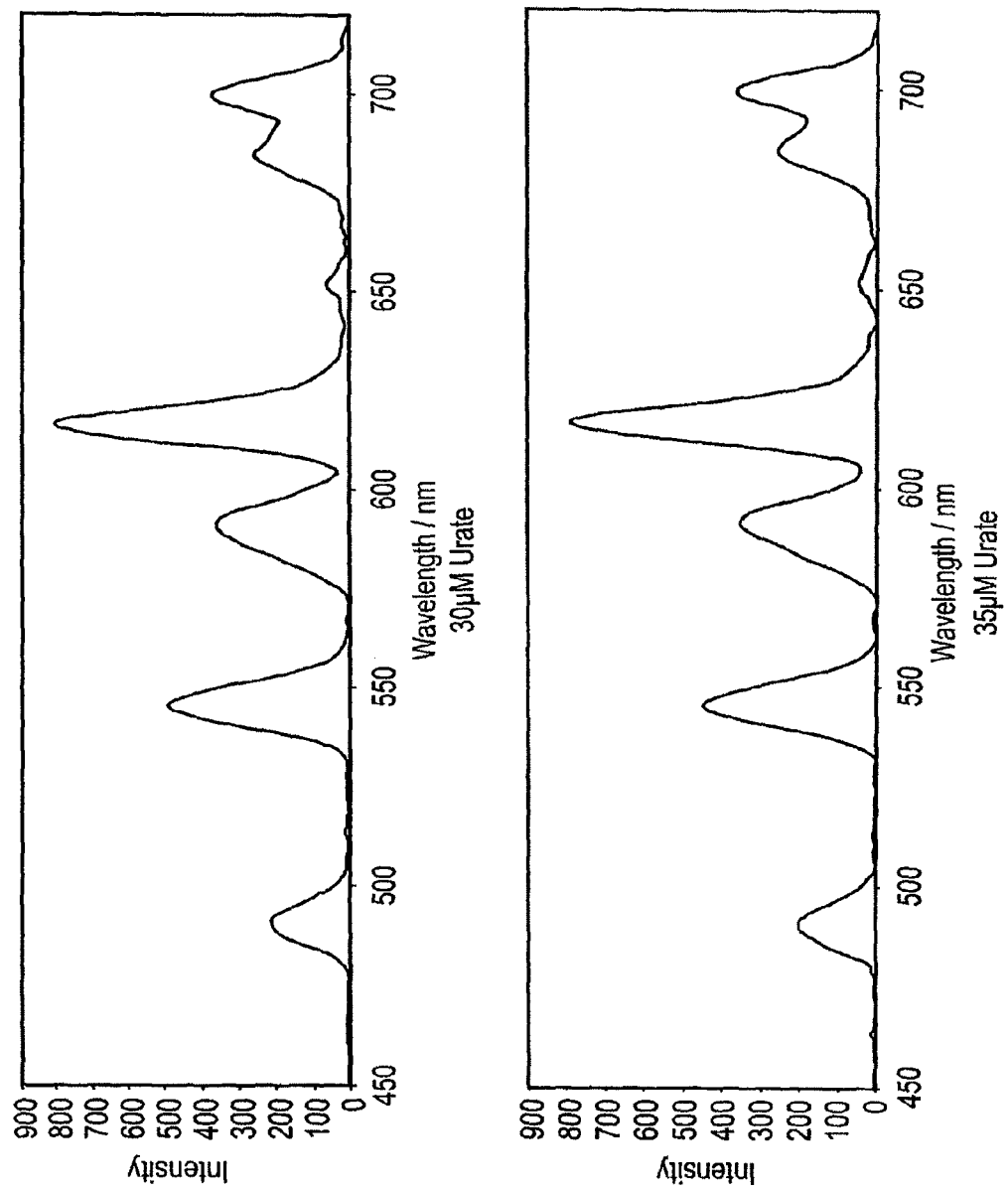
Figure 3E:
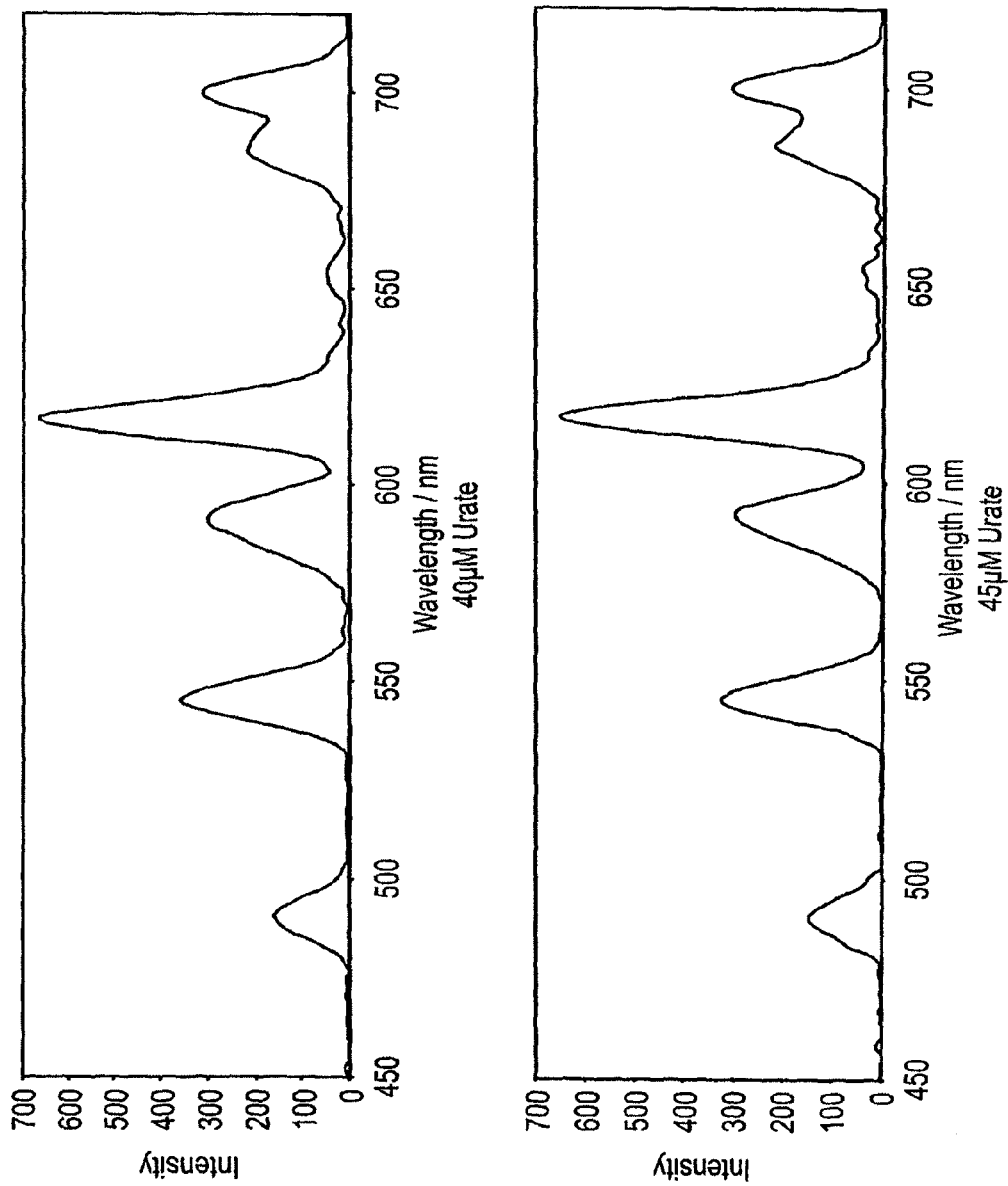
Figure 3F:
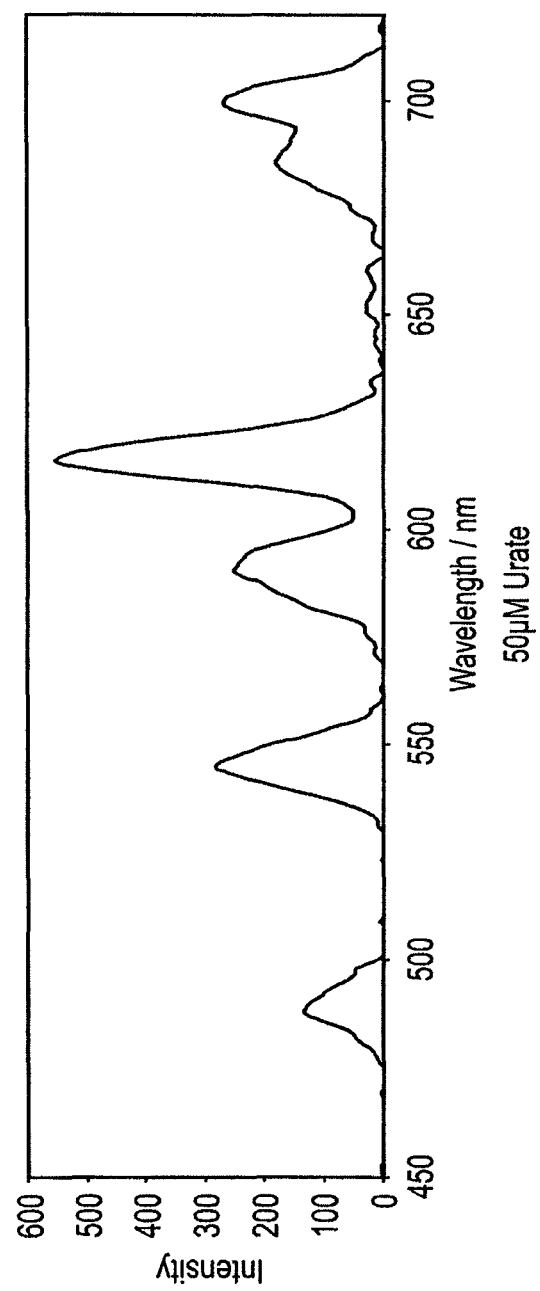

The assay of this invention utilises luminescent lanthanide (III) complexes, in particular of lanthanide (III) ions such as europium, dysprosium, samarium, terbium, neodymium or ytterbium, more particularly europium, dysprosium, samarium or terbium, still more particularly europium and terbium, based on a common ligand, with differing sensitivity to quenching of the lanthanide excited state by reductants; and their application in assays of compounds with a low oxidation potential.

In one embodiment, the invention provides a non-enzymatic method for determining the concentration of uric acid, as urate, in diluted serum or optionally diluted urine. It should be noted, however, that whilst invention is described herein with particular reference to the analysis of uric acid, as urate, and highlights the issue of ascorbate interference in such analyses, the invention is equally applicable to the analysis of other reductants of biological interest that show a pronounced tendency to quench the lanthanide excited state of a given pair of lanthanide ions to differing extents. As examples of such analytes, ascorbate is of clinical importance: a deficiency of vitamin C (i.e. ascorbic acid) can lead to the disease scurvy. The recommended daily intake of vitamin C is 60 mg with typical plasma levels being of the order 3 to 20 mg/L in healthy patients. Vitamin C deficiency can also occur amongst smokers; chronic diseases such as alcoholism and cancer can result in hypovitaminosis. The group of patients most susceptible to scurvy are women, when plasma levels of vitamin C fall below 2 mg/L.

In addition to urate and ascorbate, a vast number of phenolic compounds are of biological interest. For example phenolic compounds (including catechols and catecholmines) are often found as hormones, vitamins and food antioxidants. Many food antioxidants in particular are phenolic compounds and a simple and efficient analytical method of determining concentrations of such compounds is thus of clear utility.

We have surprisingly found that lanthanide (III) complexes such as those described herein can be used directly in assays of bioactive species in biological samples, such as bodily fluids, including time-resolved assays, especially in signalling the variation in the local concentration of endogenous electron-rich species, such as uric acid (as its conjugate base, urate). Complexes of two different lanthanide ions should a priori exhibit differing sensitivity to quenching of the lanthanide excited state, by a process involving electron transfer. In particular, the invention relates to the use of two luminescent lanthanide (III) complexes, derived from a common ligand, incorporating, for example, an azaxanthone, azathioxanthone or a tetraazatriphenylene sensitising moiety capable of co-ordinating to a lanthanide ion by one or more nitrogen atoms. By sensitising moiety is meant an entity that absorbs light efficiently (as defined by an extinction coefficient of greater than 1000 liter$^{-1}$ moles$^{-1}$cm$^{-1}$) and possesses an energy that is more than 2000 cm$^{-1}$ above the energy of the lowest excited state of the emissive lanthanide ion and hence can act as a donor in an energy transfer process to allow population of the lanthanide excited state. The replacement of one lanthanide ion by another in a complex with a ligand is simply undertaken, and two or more such of complexes may be expected normally to possess very similar chemical properties.

Complexes of europium and terbium, in particular, with the macrocyclic ligands described herein exhibit a very different sensitivity to quenching of the lanthanide excited state by sodium urate, and surprisingly, selected complexes are much less sensitive to quenching by other low molecular reductants, such as ascorbate. By appropriate selection of the common ligand the resultant complexes of the lanthanide ions (particularly Tb and Eu) bind only weakly to proteins. Therefore, the effect of quenching by urate is also not normally subject to significant interference from the presence of proteins or indeed related biomolecules present in the analyte of interest.

In the method of this invention, each of the two or more different macrocyclic lanthanide (III) complexes are sensitive to differing extents, to quenching of their metal-centred excited states by an electron-rich donor, typically an anionic species with a low oxidation potential. As a result, the emission spectral response of a solution containing mixtures of complexes of two or more lanthanide ions (preferably two) is modulated, allowing analysis of the spectral signal as a function of the concentration of the quenching species, by monitoring the intensity of two or more emission wavelengths, or by monitoring changes in emission lifetime at two or more of these wavelengths. Thus, by the provision of two or more lanthanide (III) complexes of a common ligand, wherein each complex exhibits a different sensitivity to quenching of the lanthanide excited state by readily oxidised compounds, such as low molecular weight anti-oxidants (e.g. urate, ascorbate) found in biological fluids, the amount of such analytes present in such fluids may be easily determined.

Because the assay typically involves two complexes of a common ligand, other non-specific effects that may perturb the observed emission intensity or lifetime for a given sample (e.g. temperature, light scattering due to particulates, surface effects, varying concentrations in a given sample of other reducing agents, protein adhesion) occur to the same effect in each case. Consequentially, by taking a ratio of two emission intensities, or emission lifetimes, from each lanthanide, these effects cancel out, enhancing the inherent precision of the method. Thus, the method is ratiometric and obviates any sample/sample variability that might otherwise compromise a method based on modulation of spectral emission using only one complex.

As noted herein the various aspects of the invention relate to macrocyclic lanthanide (III) complexes, that is complexes formed between lanthanide (III) ions and macrocyclic ligands. Particularly preferred macrocycles are based upon 1,4,7,10-tetraazacyclododecane capable of chelating to a bound lanthanide ion through the four nitrogen atoms of the tetraazacyclododecane ring. The skilled person will be aware how to construct the macrocyclic lanthanide (III) complexes used according to the various aspects of this invention. In the literature, examples of methods appropriate to the synthesis of macrocyclic ligands and their complexes may be found, for example, in D. Parker et al., *Org. Biomol. Chem.*, 2005, 3, 1013 and in "Azaxanthones and azathioxanthones as sensitisers for europium and terbium luminescence", *Org Biomol. Chem.*, 2006, 4, 1707-1722 (D. Parker P. A. Atkinson, K. S. Findlay, F. Kielar, R. Pal, R. A. Poole, H. Puschmann, S. L. Richardson, P. A. Stenson, A. L. Thompson and J. Yu).

The compounds of the present invention preferably each comprise azaxanthone, azathioxanthone, or tetraazatriphenylene sensitising moieties, capable of co-ordinating to a lanthanide ion by one or more nitrogen atoms of an integral pyridyl group or a related moiety, such as C—OH or N-oxide. Preferably the macrocyclic ligand is based upon a 1,4,7,10-tetraazacyclododecane ring, substituted at position 1 with a sensitising moiety and with three additional ligating groups bound to the 4, 7 and 10 nitrogen atoms of the 1-substituted 12-ring macrocycle. These additional groups may be permuted in order to modulate the sensitivity of the derived lanthanide (III) complexes to collisional deactivation by quenching electron-rich species.

Preferably, the macrocyclic ligands are of the general structures 1-4 shown below:

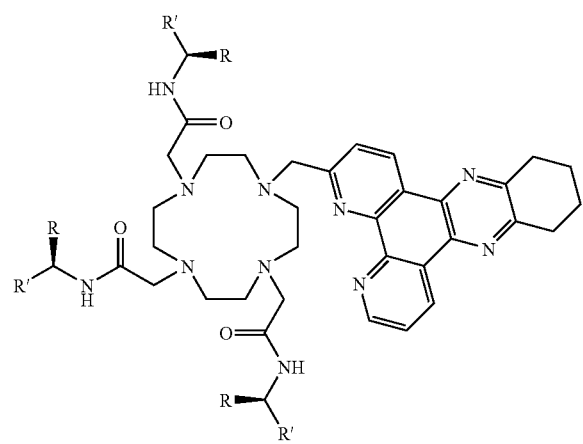

1

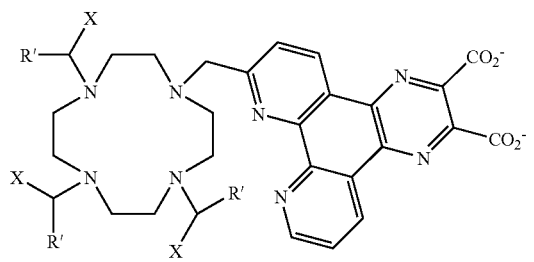

2

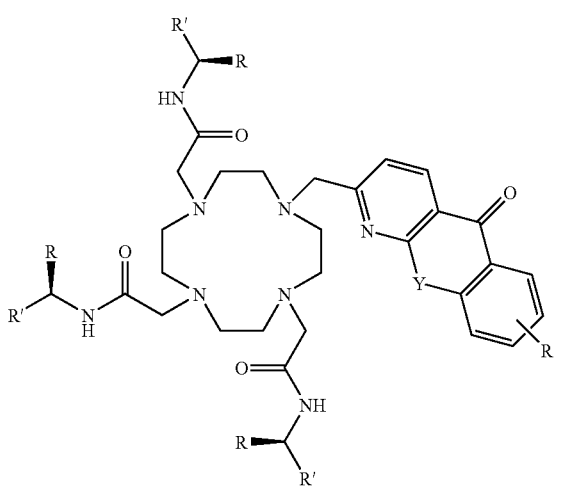

3

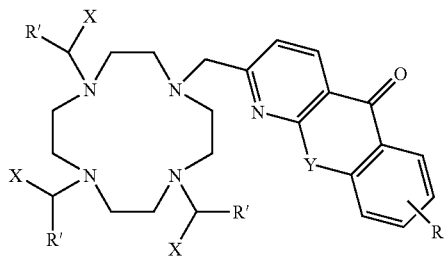

4 wherein
R=H, $CO_2^-$, $CO_2R'$, $CONHR'$, $NHCOR'$, $C_{1-6}$ straight-chain, branched, cyclo- or cycloalkyl-alkyl, preferably methyl or ethyl, Ph or $CH_2Ph$;
R'=H, $C_{1-6}$ straight-chain, branched, cyclo- or cycloalkyl-alkyl, preferably methyl, ethyl, propyl or butyl, Ph, $CH_2Ph$, $(CH_2)_nCO_2^-$ wherein n=1, 2, 3 or 4;
X=$CO_2^-$, $PR''O_2^-$ or $PO_2(OR'')^{2-}$ wherein R''=H, $C_{1-6}$ straight-chain, branched, cyclo- or cycloalkyl-alkyl, preferably methyl, ethyl, propyl or butyl, Ph or $CH_2Ph$; and
Y=O or S.

Alternatively, the macrocyclic ligands may be of the general structure 1a shown below:

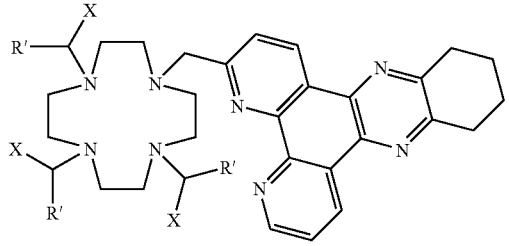

1a wherein
R'=H, $C_{1-6}$ straight-chain, branched, cyclo- or cycloalkyl-alkyl, preferably methyl, ethyl, propyl or butyl, Ph, $CH_2Ph$, $(CH_2)_nCO_2^-$ wherein n=1, 2, 3 or 4; and
X=$CO_2^-$, $PR''O_2^-$ or $PO_2(OR'')^{2-}$ wherein R''=H, $C_{1-6}$ straight-chain, branched, cyclo- or cycloalkyl-alkyl, preferably methyl, ethyl, propyl or butyl, Ph or $CH_2Ph$.

It will be understood from the foregoing that, in the compounds of formula 1 to 4 (and 1a) above (and in 5 to 7 (and 10) below), the pyridyl nitrogen atoms shown may be replaced with moieties capable of chelation to a bound lanthanide ion, such as C—OH and N—O.

The macrocyclic ligands discussed herein may be used to provide luminescent lanthanide (III) complexes by binding to a lanthanide ion, preferably europium (III) and terbium (III). Exemplary of such complexes are those shown below in structures 5, 6 and 7:

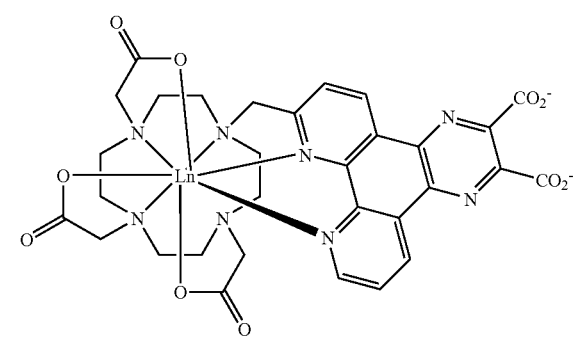

5

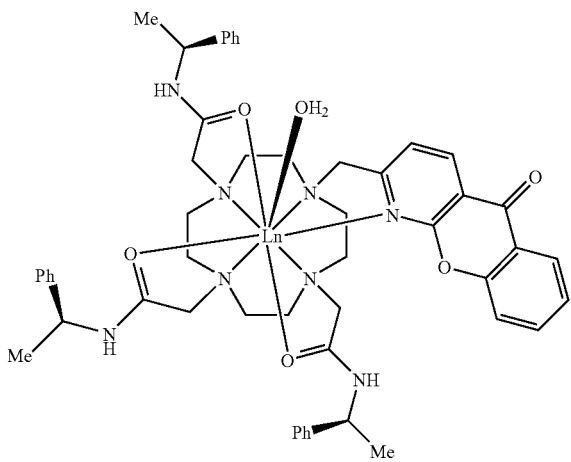

6

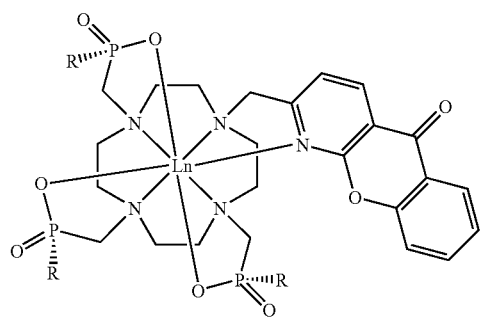

7 wherein

Ln is the lanthanide (III) ion (preferably terbium or europium); and

R is Me or CH$_2$Ph; and

10:

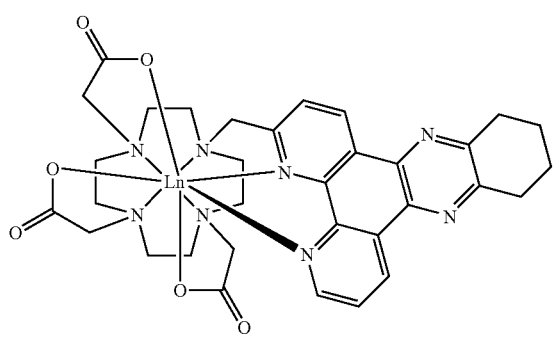

wherein Ln is the lanthanide (III) ion (preferably terbium or europium).

The macrocyclic lanthanide (III) complexes described herein, e.g. 5-7 and 10, are prone to quenching by electron transfer of their long-lived excited states. This quenching process may be characterised in homogeneous solution by a Stern-Volmer quenching constant, $K_{SV}^{-1}$, whose value (units typically mM) indicates the concentration of the quenching species required to diminish the emission intensity to 50% of the original value. With complex 6, for example, the values of $K_{SV}^{-1}$, for the terbium complex are 0.04 mM (urate) and 0.37 mM (ascorbate), compared to 0.6 mM and 1.5 mM respectively for the europium analogue. Similarly with 5, the terbium complexes are much more sensitive to urate quenching than ascorbate (values of $K_{SV}^{-1}$ are 0.01 and 0.16 mM for urate quenching for the Tb and Eu complex respectively; cf. 0.75 mM and 4.31 mM for ascorbate quenching). Such behaviour allows for the direct analysis of the concentration of urate in solution, by comparing the ratio of the emission intensity of a Tb emission band (e.g. 546 nm) relative to the intensity of a (preferably non-overlapping) Eu emission band e.g. at 700 nm. The ratio of the intensity of these bands is then and may be used as a direct function of urate concentration, provided that interfering quenching species contribute very little to the overall quenching effect, i.e. are much less effective quenchers.

Thus, in order to calculate the amount of urate (or other analyte of interest) in any given sample, the analytical process is normally conducted with a solution containing a mixture of two or more macrocyclic lanthanide (III) complexes with a common ligand, and, where terbium and europium complexes are used, monitoring of the ratio of the Tb/Eu emission intensities or lifetimes (preferably intensities), in particular the 546/616 or 546/700 nm bands. By preparing a series of solutions containing known concentrations of the analyte concerned, a series of solutions may be prepared from which a calibration plot is obtained. An example of this is described in Example 4 below.

The various aspects of this invention are of general utility in or in relation to the analysis of samples, particularly of biological fluids. In addition to the preferred fluids which may be analysed according to the method of this invention, other such fluids which may be analysed include blood, plasma, saliva, mucus, perspiration, lymph, gastric juice, aqueous humor and semen; or synovial, amniotic, pericardial, peritoneal, pleural, cerebrospinal, vaginal and faecal fluids.

It should be noted again that the method of this invention is applicable to the analysis of a variety of analytes having low oxidation potential. The analytes have an oxidation potential, for a one electron oxidation process, of about +0.10 to about +1.20 volts, at pH 7 (relative to the normal hydrogen electrode at 298 K), preferably +0.25 to about +0.75 V. (Urate according to this scale has a value of 0.59 V and ascorbate a value of +0.30 V).

Whilst it may be appreciated from the foregoing discussion of the relative $K_{sv}^{-1}$ values for urate and ascorbate that the quantification of ascorbate in the presence of urate will be problematic, this difficulty is easily alleviated by the treatment of the biological fluid which is to be analysed with a uricase enzyme to degrade the uric acid. The ascorbate may then be analysed without interference from uric acid.

The invention is now illustrated in more detail by the following examples, which are not to be considered as limiting of the invention. They describe the synthesis and characterisation of representative common ligands, 2, 3 and 4, and their Eu and Tb complexes; the synthetic methods employed will be evident to those skilled in the art. An example of the analysis of a urine sample (Example 4) is also given; Example 5 describes quenching by selected catechols and protected catechols.

Example 1

Ligand 3 and Complex 6

1-(2-Methyl-1-azaxanthone)-4,7,10-tris[(S)-1-(1-phenyl)ethylcarbamoylmethyl]-1,4,7,10-tetraazacyclododecane, 3

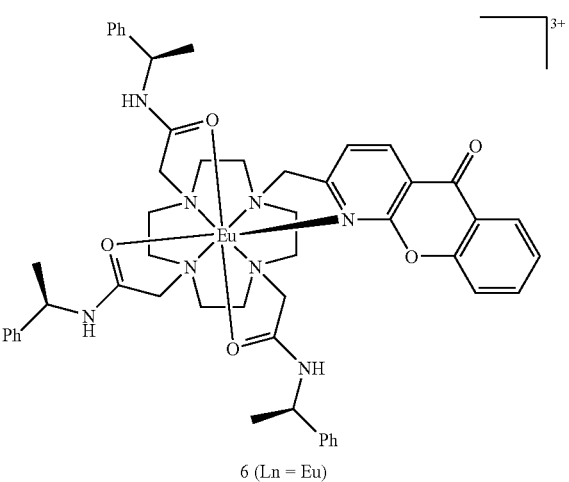

6 (Ln = Eu)

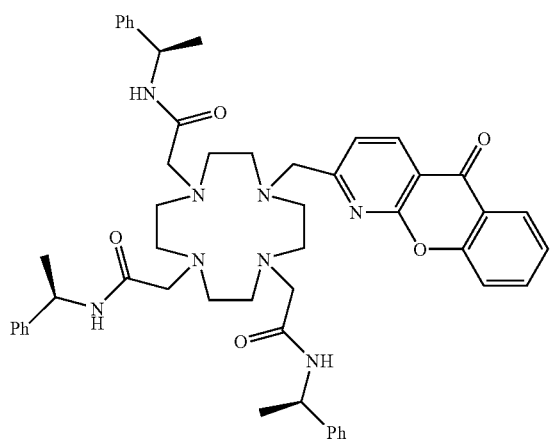 [SMILES: C[C@H](NC(=O)CN1CCN(CC(=O)N[C@H](C)c2ccccc2)CCN(CC(=O)N[C@H](C)c2ccccc2)CCN(Cc2ccc3c(=O)c4ccccc4oc3n2)CC1)c1ccccc1]

2-Methyl-1-azaxanthone-1,4,7,10-tetraazacyclododecane (130 mg, 0.34 mmol), $K_2CO_3$ (236 mg, 1.70 mmol) and KI (4 mg) were dissolved in acetonitrile (10 ml) and the orange solution heated to 60° C. under argon. (S)-N-(1-phenylethyl) chloroacetamide (269 mg, 1.36 mmol, 4 equivalents) in DCM (10 ml) was added, and the reaction mixture refluxed at 60° C. for 60 hours. On cooling the solution was filtered and washed with DCM. The solution was then washed with water and dried ($K_2CO_3$). Removal of the solvent under reduced pressure yielded a crude brown oil which was purified via column chromatography (alumina, DCM→0.4% MeOH:DCM) yielding the title compound as an orange crystalline solid (208 mg, 70%), m.p. 112-113° C. $\delta_H$ (CDCl$_3$) 1.45 (9H, m, 3×CH$_3$), 2.91 (22H, m br, 8× cyclen CH$_2$ and 3×NCH$_2$CO), 3.79 (2H, s br, CH$_2$-AzaH), 4.74 (1H, m br, PhCH), 5.00 (2H, m br, 2×PhCH), 7.20 (16H, m, 3×Ph and H$^7$), 7.42 (1H, m, H$^9$), 7.60 (1H, m, H$^3$), 7.78 (1H, m, H$^8$), 8.31 (1H, m, H$^6$), 8.56 (1H, m, H$^4$). m/z (ESMS$^+$) 453 (M+Ca, 20%), 464 (M+K+Na, 40%), 866 (M+H, 40%), 888 (M+Na, 100%). HRMS (ES$^+$), found: 887.4582 (M+Na); C$_{51}$H$_{60}$N$_8$O$_5$Na requires 887.4579

1-(2-Methyl-1-azaxanthone)-4,7,10-tris[(S)-1-(1-phenyl) ethylcarbamoylmethyl]-1,4,7,10-tetraazacyclododecane (30 mg, 0.035 mmol) and Eu(OTf)$_3$ (21 mg, 0.035 mmol) were dissolved in CH$_3$CN (5 ml). The solution was stirred at 80° C. for 60 hours under argon. The solvent was then removed under reduced pressure, and the brown oil redissolved in a minimum of acetonitrile and added dropwise to diethyl ether (60 ml) yielding a fine precipitate. The product was centrifuged and the process repeated. An ion exchange was then performed on a DOWEX resin. The complex was obtained as a colourless solid (24 mg, 69%), m.p.>250° C. $\delta_H$ (CD$_3$OD) partial assignment (tentative assignment): −19.96 (1H, s, NCH$_2$CO), −18.05 (1H, s, H$^2$eq'), −17.72 (1H, s, NCH$_2$CO), −15.13 (2H, s, 2×NCH$_2$CO), −12.97 (1H, s, H$^4$eq'), −11.80 (1H, s, H$^2$eq'), −10.95 (1H, s, H$^4$ax"), −10.55 (1H, s, Heq), −10.28 (1H, s, H$^1$ax"), −9.88 (1H, s, NCH$_2$CO), −8.20 (1H, s, H$^4$eq"), −6.06 (1H, s, NCH$_2$CO), −5.03 (1H, s, H$^3$eq"), −4.85 (1H, s, H$^2$ax"), −4.85 (1H, s, H$^1$eq"), −2.71 (3H, d, CH$_3$), −2.67 (1H, s, H$^3$ax"), −1.92 ($\delta_H$, d, 2×CH$_3$), −0.41 (1H, s, H$^3$eq'), 7.99 (1H, s, H$^1$eq'), 5.79-11.86 (26H, AzaH, CH$_2$-AzaH, 3×PhCH, 3×Ph), 13.77 (1H, s, H$^4$ax'), 20.58 (1H, s, H$^3$ax'), 21.62 (1H, s, H$^2$ax'), 31.15 (1H, s, H$^1$ax'). m/z (ESMS$^+$) 517 (M$^{3+}$+F$^-$, 100%). HRMS (ES$^+$), found: 517.1926 (M$^{3+}$+F$^-$); C$_{51}$H$_{60}$N$_8$O$_5$EuF requires 517.1929; $\lambda_{ex}$ (H$_2$O): 335 nm; $\tau_{H2O}$: 0.54 ms; $\tau_{D2O}$: 1.73 ms; $\phi_{H2O}$: 0.08

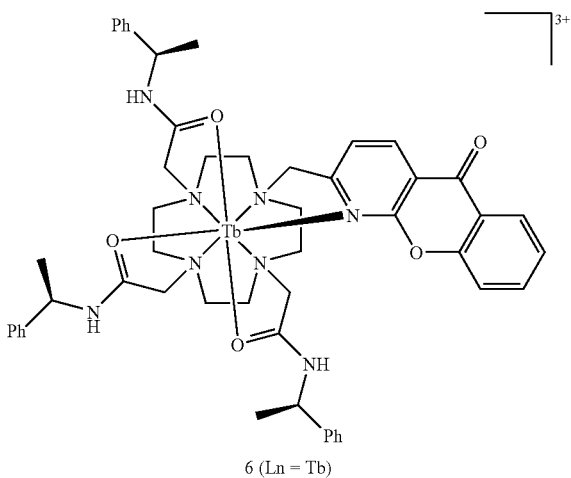

6 (Ln = Tb)

1-(2-Methyl-1-azaxanthone)-4,7,10-tris[(S)-1-(1-phenyl) ethylcarbamoylmethyl]-1,4,7,10-tetraazacyclododecane (50 mg, 0.058 mmol) and Tb(OTf)$_3$ (35 mg, 0.058 mmol) were dissolved in CH$_3$CN (5 ml). The solution was stirred at 80° C. for 60 hours under argon. The solvent was then removed under reduced pressure, and the brown oil redissolved in a minimum of acetonitrile and added dropwise to diethyl ether (60 ml) yielding a fine precipitate. The product was centrifuged and the process repeated. An ion exchange was performed on a DOWEX resin. The complex was obtained as a pale yellow solid (35 mg, 59%), m.p.>250° C. m/z (ESMS$^+$) 521 (M$^{3+}$+F$^-$, 100%). HRMS (ES$^+$), found: 521.1949 (M$^{3+}$+F); C$_{51}$H$_{60}$N$_8$O$_5$TbF requires 521.1957; $\lambda_{ex}$ (H$_2$O): 335 nm; $\tau_{H2O}$: 1.65 ms; $\tau_{D2O}$: 2.89 ms; $\phi_{H2O}$: 0.37.

Example 2

Synthesis of 2 (R'=H) and 5

Diethyl 7-carboxaldehyde-dipyrido[3,2-f:2',3'-h] quinoxaline-2,3-dicarboxylate

Selenium dioxide (480 mg, 4.33 mmol) was added to the solution of diethyl 7-methyldipyrido[3,2-a:2',3'-c]quinoxaline-2,3-dicarboxylate (810 mg, 2.07 mmol) in dioxane (170 ml). The mixture was boiled under reflux for 4 h and was allowed to cool down afterwards. The reaction mixture was filtered through a Celite plug. The solvent was removed under reduced pressure to give the crude product, which was used without further purification. $^1$H NMR (200 NMR, CDCl3$_3$): δ 1.52 (6H, t, J=7.2, OCH$_2$CH$_3$), 4.60 (4H, q, J=7.2, OCH$_2$), 7.92 (1H, dd, J=8.6, 4.6, H11), 8.46 (1H, d, J=8.2, H5), 9.43 (1H, dd, J=4.4, 1.8, H10), 9.61 (1H, dd, J=8.2, 1.8, H12), 9.74 (1H, dd, J=8.4, 0.8, H6), 10.60 (1H, d, J=1.0, COH). $^{13}$C NMR (75 MHz, CDCl$_3$): δ 14.2 (CH$_3$), 63.3 (CH$_2$), 121.7 (C5), 125.0 (C11), 126.8 (q Ar), 129.2 (q Ar), 134.7 (C12), 136.0 (C6), 139.5 (q Ar), 141.2 (q Ar), 144.5 (q Ar), 145.3 (q Ar), 147.8 (q Ar), 148.4 (q Ar), 153.9 (C10), 154.8 (C7), 164.6 (CO ester), 164.7 (CO ester), 193.7 (CO aldehyde).

Diethyl 7-(hydroxymethyl)dipyrido[3,2-f:2',3'-h] quinoxaline-2,3-dicarboxylate

Sodium cyanoborohydride (130 mg, 2.07) was added to a solution of diethyl 7-carboxaldehyde-dipyrido[3,2-f:2',3'-h] quinoxaline-2,3-dicarboxylate (840 mg, 2.07 mmol) CHCl$_3$-EtOH 7:1 (105 ml). The reaction mixture was boiled under reflux for 4 h. The reaction mixture was poured into concentrated Na$_2$CO$_3$ (150 ml). The organic phase was separated and the water layer was extracted by CHCl$_3$ (4×120 ml). The organic layer was dried over K$_2$CO$_3$. The solvent was removed under reduced pressure to give the crude product, which was obtained by recrystallisation from CHCl$_3$/Hexane as pale yellow-green solid (400 mg, 0.98 mmol, 48%). $^1$H NMR (300 MHz, CDCl3): δ 1.51 (6H, t, J=7.2, OCH$_2$CH$_3$), 4.59 (4H, q, J=7.2, OCH$_2$), 5.24 (2H, s, CH$_2$OH), 7.83 (1H, dd, J=8.1, 4.5, H11), 7.94 (1H, d, J=8.4, H6), 9.30 (1H, dd, J=4.5, 1.8, H10), 9.53 (1H, d, J=9.3, H5), 9.60 (1H, dd, J=8.1, 1.8, H12). $^{13}$C NMR (75 MHz, CDCl$_3$): δ 14.4 (CH$_3$), 63.1 (OCH$_2$), 66.0 (CH$_2$OH), 121.9 (C6), 124.5 (C11), 125.3 (qAr), 126.5 (qAr), 134.6 (C12), 135.1 (C5), 140.0 (q Ar), 140.4 (qAr), 144.0 (qAr), 144.4 (qAr), 147.5 (qAr), 148.0 (qAr), 153.4 (C10), 164.7 (C7), 164.9 (CO), 165.0 (CO). m/z (ES$^+$) 429 (MNa$^+$).

Diethyl 7-(chloromethyl)dipyrido[3,2-f:2',3'-h]quinoxaline-3,2-dicarboxylate

Phosphorus trichloride (473 mg, 3.44 mmol) was added to a solution diethyl 7-(hydroxymethyl)dipyrido[3,2-f:2',3'-h] quinoxaline-2,3-dicarboxylate (350 mg, 0.86 mmol) in CHCl$_3$ (150 ml). The reaction mixture was heated under reflux for 6 h and allowed to cool down to room temperature afterwards. The reaction was quenched by addition of concentrated Na$_2$CO$_3$ solution (150 ml). The layers were separated and the water was extracted by CH$_2$Cl$_2$ (3×150 ml) and CHCl$_3$ (1×50 ml). The organic layer was dried over K$_2$CO$_3$. The solvent was removed under reduced pressure to give the crude product. Purification was achieved by chromatography on alumina (gradient elution: CH$_2$Cl$_2$ to 2% CH$_3$OH—CH$_2$Cl$_2$) The product was obtained as a yellow glass (95 mg, 0.22 mmol, 26%). $^1$H NMR (300 MHz, CDCl3): δ 1.45 (6H, t, J=7.2, OCH$_2$CH$_3$), 4.53 (4H, q, J=7.2, OCH$_2$), 5.07 (2H, s, CH$_2$Cl), 7.78 (1H, dd, J=8.1, 4.5, H11), 8.05 (1H, d, J=8.4, H6), 9.31 (1H, dd, J=4.5, 1.8, H10), 9.50 (1H, dd, J=8.1, 1.8, H12), 9.53 (1H, d, J=8.7, H5). $^{13}$C NMR (75 MHz, CDCl$_3$): δ14.4 (CH$_3$), 47.3 (CH$_2$Cl), 63.2 (OCH$_2$), 123.8 (C11), 124.6 (C6), 125.6 (q Ar), 126.6 (q Ar), 134.5 (C12), 135.7 (C5), 140.1 (qAr), 140.4 (qAr), 144.3 (q Ar), 144.4 (qAr), 147.6 (q Ar), 148.1 (qAr), 153.8 (C10), 161.0 (C7), 165.0 (CO), 165.1 (CO). m/z (ES$^+$) 447 (MNa$^+$).

1-(Diethyl-7'-methyldipyrido[3,2-f:2',3'-h]quinoxaline-2,3-dicarboxylate)-4,7,10-tris-tert-butoxycarbonylmethyl-1,4,7,10-tetraazacyclododecane Potassium carbonate (11 mg, 0.079 mmol) and a catalytic amount of KI were added to a solution of 1,4,7-tris-tert-butoxycarbonylmethyl-1,4,7,10-tetrataazacyclododecane (40 mg, 0.077 mmol) and diethyl-7-(chloromethyl)dipyrido[3,2-f:2',3'-h]quinoxaline-2,3-dicarboxylate (35 mg, 0.083 mmol) in acetonitrile (5 ml). The mixture was heated under reflux overnight, under argon. The solution was filtered and the salts were washed with CH$_2$Cl$_2$. The solvent was removed under reduced pressure to give the crude product. Purification was achieved by chromatography on alumina (gradient elution: CH$_2$Cl$_2$ to 2% CH$_3$OH—CH$_2$Cl$_2$). The product was obtained as a yellow glass (40 mg, 0.44 mmol, 56%). $^1$H NMR (200 MHz, CDCl$_3$): δ 1.08 (18H, s, CH$_3$), 1.43 (9H, s, CH$_3$), 1.50 (3H, t, J=7.2, CH$_3$), 1.51 (3H, t, J=7.2, CH$_3$), 2.25-3.58 (24H, br m, CH$_2$ ring, NCH$_2$), 4.58 (2H, q, J=7.2, OCH$_2$), 4.59 (2H, q, J=7.2, OCH$_2$), 7.84 (1H, d, J=8.4, H6), 7.86 (1H, dd, J=8.2, 4.4, H11), 8.98 (1H, dd, J=4.4, 1.8, H10), 9.53 (1H, d, J=8.4, H5), 9.59 (1H, dd, J=8.2, 1.8, H12). $^{13}$C NMR (75 MHz, CDCl$_3$): δ 14.4 (OCH$_2$CH$_3$), 28.0 (CH$_3$), 28.3 (CH$_3$), 56.4-60.8 (CH$_2$ ring), 63.3 (OCH$_2$), 81.9-82.8 (CH$_2$CO, CH$_2$), 124.5 (C6), 124.7 (C11), 125.2 (q Ar), 126.7 (q Ar), 134.9 (C12), 135.2 (C5), 139.9 (q Ar), 140.2 (q Ar), 144.2 (q Ar), 144.7 (q Ar), 147.3 (q Ar), 147.7 (q Ar), 153.3 (C10), 163.2 (C7), 164.8 (COOEt), 164.9 (COOEt), 173.0 (CO). m/z (ES$^+$) 926 (MNa$^+$).

5 (Ln=Tb)

A solution of 1-(diethyl-7'-methyldipyrido[3,2-f:2',3'-h]quinoxaline-2,3-dicarboxylate)-4,7,10-tris-tert-butoxycarbonylmethyl-1,4,7,10-tetraazacyclododecane (50 mg, 55 μmol) in 6 M HCl (10 ml) was heated under reflux overnight. The solvent was removed under reduced pressure to give the product. The product was checked by $^1$H NMR to ensure complete ester hydrolysis, and was used for complexation immediately. $^1$H NMR (300 MHz, CD$_3$OD): δ 2.90-4.00 (24H, br m, CH$_2$), 8.62 (2H, m, C6, C11), 9.57 (2H, m, C5, C12), 10.34 (H, d, J=8.1, H10). The ligand was dissolved in a mixture of methanol and water (1:1, 6 ml) and the pH was raised to 5.5 by addition of a 1 M solution of aqueous KOH solution. TbCl$_3$.6H$_2$O (22 mg, 59 μmol) was added and the mixture heated at 90° C. for 48 h. The pH was readjusted to 5.5 after 24 h by 1M solution of KOH. The solvents were removed under reduced pressure. The residue was dissolved water and the pH was adjusted to 7.0 by 1 M solution of KOH and ion exchange was performed on a weakly acidic resin. The solution was freeze-dried to yield a white solid, which was purified by reverse phase HPLC. The solvent was removed under reduced pressure to give the product as a white solid (12 mg, 14 μmol, 24%). λ$_{abs}$ (H$_2$O) 347 nm; τ (H$_2$O) 1.80 ms. HRMS (ES$^-$): found: 833.1339 [M−H]; C$_{31}$H$_3$N$_8$O$_{10}$ $^{159}$Tb requires 833.1344.

5 (Ln=Eu)

A solution of 1-(Diethyl-7'-methyldyprido[3,2-f:2',3'-h]quinoxaline-2,3-dicarboxylate)-4,7,10-tris-tert-butoxycarbonylmethyl-1,4,7,10-tetraazacyclododecane (50 mg, 55 μmol) in 6 M HCl (10 ml) was heated under reflux overnight. The solvent was removed under reduced pressure to give the product. The product was checked by $^1$H NMR to ensure complete ester hydrolysis, and was used for complexation immediately. $^1$H NMR (300 MHz, CD$_3$OD): δ 2.90-4.00 (24H, br m, CH$_2$), 8.62 (2H, m, C6, C11), 9.57 (2H, m, C5, C12), 10.34 (H, d, J=8.1, H10). The ligand was dissolved in a mixture of methanol and water (1:1, 6 ml) and the pH was raised to 5.5 by addition of a 1 M solution of KOH. EuCl$_3$.6H$_2$O (22 mg, 60 μmol) was added and the mixture heated at 90° C. for 48 h. The pH was readjusted to 5.5 after 24 h by 1M solution of KOH. The solvents were removed under reduced pressure. The residue was dissolved water and the pH was adjusted to 7.0 by 1 M solution of KOH and ion exchange was performed on a weakly acidic resin. The solution was freeze dried to yield a white solid, which was purified by reverse phase HPLC. The solvent was removed under reduced pressure to give the product as a white solid (10 mg, 12 μmol, 22%). λ$_{abs}$ (H$_2$O) 347 nm; τ$_{Eu}$ (H$_2$O) 1.0 ms. HRMS (ES$^-$): found: 825.1285 [M−H]; C$_{31}$H$_{30}$N$_8$O$_{10}$ $^{151}$Eu requires 825.1289.

Example 3

Synthesis of 4 (R'=H) and 7

1,4,7-tris(benzyl-ethyloxyphosphinatomethyl)-10-tert-butyoxycarbonyl-1,4,7,10-tetraazacyclododecane Benzyl diethoxyphosphine (1.4 g, 6.6 mmol) was added to a mixture of 1-tert-butoxycarbonyl-1,4,7,10-tetraazacyclododecane (0.4 g, 1.47 mmol) and paraformaldehyde (0.3 g) in dry THF (23 ml). The reaction mixture was heated to reflux for 8 hours. The reaction mixture was filtered and the solvent was removed under reduced pressure. The residue was purified by column chromatography on alumina (CH$_2$Cl$_2$ to 6% MeOH) to yield the product as an oil (0.3 g, 24%). $^1$H NMR (300 MHz, CDCl$_3$): δ1.18 (9H, m, CH$_3$), 1.39 (9H, s, C(CH$_3$)$_3$), 2.60-3.80 (28H, m, NCH$_2$, PCH$_2$), 3.95 (6H, m, OCH$_2$), 7.30 (15H, m, phenyl). $^{31}$P NMR (120 MHz): δ 50.31 (P). m/z (ES$^+$) 883.4 (M+Na$^+$).

1,4,7-tris(benzyl-ethyloxyphosphinatomethyl)-1,4,7,10-tetraazacyclododecane

A solution of 1,4,7-tris(benzyl-ethyloxyphosphinatomethyl)-10-tert-butyoxycarbonyl-1,4,7,10-tetraazacyclododecane (450 mg, 0.523 mmol) in CH$_2$Cl$_2$ (10 ml) and TFA (20 ml) was stirred at room temperature under argon atmosphere overnight. The solvent was removed under reduced pressure. The residue was dissolved in CH$_2$Cl$_2$ and saturated K$_2$CO$_3$ solution. The product was extracted into CH$_2$Cl$_2$. The combined organic extracts were dried over K$_2$CO$_3$ and the solvent was removed under reduced pressure to give the product as a brown oil (330 mg, 0.434 mmol, 83%). $^1$H NMR (300 MHz, CDCl$_3$): δ 1.18 (9H, m, CH$_3$), 2.60-3.40 (28H, m, NCH$_2$, PCH$_2$), 3.90 (6H, m, OCH$_2$), 7.25 (15H, m, Phenyl). $^{31}$P NMR (120 MHz): δ 51.45 (P). m/z (ES$^+$) 761.3 (MH$^+$).

1-(2-Methylazaxanthone)-4,7,10-tris(benzyl-ethyloxyphosphinatomethyl)-1,4,7,10-tetraazacyclododecane A solution of 1,4,7-tris(benzyl-ethyloxyphosphinatomethyl)-1,4,7,10-tetraazacyclododecane (180 mg, 0.237 mmol), 2-bromomethyl-1-azaxanthone (76 mg, 0.262 mmol) and Cs$_2$CO$_3$ (77 mg, 0.236 mmol) in acetonitrile 20 ml was heated to reflux under argon atmosphere for 6 hours. The reaction mixture was filtered and the solvent was removed under reduced pressure. The residue was purified by chromatography on alumina (CH$_2$Cl$_2$ to 2% MeOH) to give the product as a brown glass (120 mg, 0.124 mmol, 52%). $^1$H NMR (300 MHz, CDCl$_3$): δ 1.13 (9H, s, CH$_3$), 2.4-3.4 (28H, bm, macrocycle, PCH$_2$, PhCH$_2$), 3.70-4.15 (8H, bm, OCH$_2$, CH$_2$), 7.26 (15H, m, Ph), 7.41 (1H, m, H$^7$), 7.55 (2H, m, H$^3$, H$^9$), 7.70 (1H, m, H$^8$), 8.28 (1H, m, H$^6$), 8.68 (1H, m, H$^4$). $^{31}$P NMR (120 MHz): δ 49.87. m/z (ES$^+$) 970.4 (MH$^+$), 992.5 (M+Na$^+$).

7 (R=Bn, Ln=Tb)

A solution of 1-(2-methylazaxanthone)-4,7,10-tris(benzyl-ethyloxyphosphinatomethyl)-1,4,7,10-tetraazacyclododecane (35 mg, 36.1 μmol) in 6 M HCl (7 ml) was heated to reflux for 24 hours. The progress of the ester hydrolysis was monitored by $^1$H and $^{31}$P NMR. The solvent was removed under reduced pressure. The residue was dissolved in water (3 ml) and MeOH (3 ml) and TbCl$_3$.6H$_2$O (15 mg, 40.2 μmol) was added. The pH of the reaction mixture was increased to 5.5 by the addition of 1 M aqueous KOH solution. The reaction mixture was heated to 60° C. overnight. The solvents were removed under reduced pressure and the residue was purified by column chromatography on alumina (CH$_2$Cl$_2$ to 10% MeOH) to give the product as a light yellow solid (10 mg, 9.6 μmol, 27%). λ$_{abs}$ (H$_2$O) 335 nm; τ$_{Tb}$ (H$_2$O) 3.50 ms, φ$_{Tb}$ 44%.

7 (R=Bn, Ln=Eu)

A solution of 1-(2-methylazaxanthone)-4,7,10-tris(benzyl-ethyloxyphosphinatomethyl)-1,4,7,10-tetraazacyclododecane (40 mg, 41.2 μmol) in 6 M HCl (6 ml) was heated to reflux for 24 hours. The progress of the ester hydrolysis was monitored by $^1$H and $^{31}$P NMR. The solvent was removed under reduced pressure. The residue was dissolved in water (3 ml) and MeOH (3 ml) and EuCl$_3$.6H$_2$O (30 mg, 81.91 mmol) was added. The pH of the reaction mixture was increased to 5.5 by the addition of 1 M KOH solution. The reaction mixture was heated to 60° C. overnight. The solvents were removed under reduced pressure and the residue was purified by column chromatography on alumina (CH$_2$Cl$_2$ to 10% MeOH) to give the product as lightly brown solid (9 mg, 8.7 µmol, 21%). $\lambda_{abs}$ (H$_2$O) 335 nm; $\tau_{Eu}$ (H$_2$O) 1.20 ms.

The corresponding methylphosphinate ligand and its Ln complexes were made in a different manner:
Trisboc AZAH A solution of 2-bromo-1-azaxanthone (50 mg, 0.172 mmol), 1,4,7-tris(tert-butoxycarbonyl)-1,4,7,10-tetraazacyclododecane (81 mg, 0.171 mmol), K$_2$CO$_3$ (95 mg, 0.687 mmol) and catalytic amount of KI in acetonitrile (5 ml) was heated to reflux overnight. The reaction mixture was filtered and salts were washed with CH$_2$Cl$_2$. The solvents were removed under reduced pressure. The residue was purified by chromatography on alumina (CH$_2$Cl$_2$ to 2% MeOH) to give the product as yellowish solid (115 mg, 0.169 mmol, 99%). $^1$H NMR (300 MHz, CDCl$_3$): δ 1.39 (9H, s, CH$_3$), 1.46 (18H, s, CH$_3$), 2.81 (4H, br m, ring CH$_2$), 3.20-3.70 (12H, br m, ring CH$_2$), 3.96 (2H, s, CH$_2$), 7.45 (1H, ddd, J 8, 7.2, 1.0, H$^7$), 7.50 (1H, d, J 8, H$^3$), 7.59 (1H, d, J 8, H$^9$), 7.75 (1H, ddd, J 8, 7.2, 1.6, H$^8$), 8.28 (1H, dd, J 8, 1.6, H$^6$), 8.59 (1H, d, J 8, H$^4$).
Cyclen AZAH A solution of 1-(2-methyl-1-azaxanthone)-4,7,10-tris(tert-butoxycarbonyl)-1,4,7,10-tetraazacyclododecane (115 mg, 0.169 mmol) in TFA (3 ml) and CH$_2$Cl$_2$ (3 ml) was stirred at room temperature under argon atmosphere overnight. The solvents were removed under reduced pressure. The residue was dissolved in CH$_2$Cl$_2$ and the solvent was removed under reduced pressure. This procedure was repeated three times. The residue was dissolved in 1 M KOH and the product was extracted into CH$_2$Cl$_2$. The combined organic extracts were dried over K$_2$CO$_3$ and the solvent was removed under reduced pressure to yield the product as a red glass (58 mg, 0.152 mmol, 90%). $^1$H NMR (300 MHz, CDCl$_3$): δ2.56 (4H, m, ring CH$_2$), 2.69 (8H, s, ring CH$_2$), 2.80 (4H, m, ring CH$_2$), 3.87 (2H, s, CH$_2$), 7.38 (1H, ddd, J 8, 7.2, 1.0, H$^7$), 7.56 (1H, dd, J 8, 1.0, H$^9$), 7.62 (1H, d, J 8, H$^3$), 7.74 (1H, ddd, J 8, 7.2, 1.6, H$^8$), 8.27 (1H, dd, J 8, 1.6, H$^6$), 8.65 (1H, d, J 8, H$^4$).
4 (R'=H, R=Me, as ethyl ester)

Diethoxymethyl phosphine (130 mg, 0.955 mmol) was added to a mixture of 1-(2-methyl-1-azaxanthone)-1,4,7,10-tetraazacyclododecane (90 mg, 0.236 mmol) and parafomaldehyde (60 mg) in THF (5 ml). The reaction mixture was heated to reflux under an argon atmosphere overnight. The reaction mixture was filtered and solvent was removed under reduced pressure. The residue was purified by chromatography on silica (CH$_2$Cl$_2$ to 2% MeOH) to yield the product as a brown glass (90 mg, 0.121 mmol, 13%). $^1$H NMR (300 MHz, CDCl$_3$): δ 1.26 (9H, m, CH$_2$CH$_3$), 1.53 (9H, m, CH$_3$), 2.5-3.3 (22H, br m, ring CH$_2$, PCH$_2$), 4.03 (8H, m, OCH$_2$, CH$_2$), 7.41 (1H, ddd, J 8, 7.2, 1.0, H$^7$), 7.58 (1H, d, J 8, H$^3$), 7.74 (2H, m, J 8, H$^9$, H$^8$), 8.29 (1H, dd, J 8, 1.6, H$^6$), 8.64 (1H, d, J 8, H$^4$).
7 (R=Me, Ln=Tb)

A solution of 1-(2-methylazaxanthone)-4,7,10-tris(methyl-ethoxyphosphinatomethyl)-1,4,7,10-tetraazacyclododecane (45 mg, 60.7 µmol) in 6 M HCl (2 ml) was heated to reflux for 24 hours. The progress of the ester hydrolysis was monitored by $^1$H and $^{31}$P NMR. The solvent was removed under reduced pressure. The residue was dissolved in water (2 ml) and MeOH (2 ml) and TbCl$_3$.6H$_2$O (30 mg, 80.3 µmol) was added. The pH of the reaction mixture was increased to 5.5 by the addition of 1 M KOH solution. The reaction mixture was heated to 60° C. overnight. The solvents were removed under reduced pressure and the residue was purified by column chromatography on alumina (69% CH$_2$Cl$_2$, 30% MeOH and 1% ammonia solution). $\lambda_{abs}$ (H$_2$O) 335 nm; $\tau_{Tb}$ (H$_2$O) 3.60 ms
7 (R=Me, Ln=Eu)

A solution of 1-(2-methylazaxanthone)-4,7,10-tris(methyl-ethyloxyphosphinatomethyl)-1,4,7,10-tetraazacyclododecane (45 mg, 60.7 µmol) in 6 M HCl (2 ml) was heated to reflux for 24 hours. The progress of the ester hydrolysis was monitored by $^1$H and $^{31}$P NMR. The solvent was removed under reduced pressure. The residue was dissolved in water (2 ml) and MeOH (2 ml) and EuCl$_3$.6H$_2$O (30 mg, 81.9 µmol) was added. The pH of the reaction mixture was increased to 5.5 by the addition of 1 M aqueous KOH solution. The reaction mixture was heated to 60° C. overnight. The solvents were removed under reduced pressure and the residue was purified by column chromatography on alumina (69% CH$_2$Cl$_2$, 30% MeOH and 1% ammonia solution). $\lambda_{abs}$ (H$_2$O) 335 nm; $\tau_{Eu}$ (H$_2$O) 1.20 ms.

Example 4

Uric Acid Assay in Urine

An exemplary ratiometric luminescence according to this invention assay comprises three elements:
1) A stock solution of pH adjusted buffer, to be used for dilution of the assay components and the uric acid containing samples.
2) A 1:1 mixture of europium(III) and terbium(III) complexes of ligand 1 (each typically giving rise a to a solution that is 5 µM concentration in each complex; R=CO$_2^-$, R'=CH$_2$CH$_2$CO$_2^-$) bearing a sensitising moiety and whose combined absorbance in a buffered aqueous solution preferably does not exceed 0.2.
3) A quantity of uric acid sufficient to make up a 1 mM solution in pH adjusted buffer: this is to be diluted in order to provide a series of solutions from which a calibration plot can be obtained.

A quantity of buffer (typically use phosphate or HEPES) is dissolved in water volumetrically to give a final concentration of 100 mM; the pH of the solution may be adjusted accordingly with either aqueous hydrochloric acid or sodium hydroxide to 7.4.

The complexes are dissolved separately in the buffer solution and their concentrations adjusted to give absorbances suitable for the sensitivity of the fluorescence multi-well plate reader or fluorimeter to be used; an absorbance of 0.1 would allow a range of detection from 500 nM-50 µM urate. The two solutions of equal absorbance are combined in equal volumes.

A series of uric acid containing solutions are prepared by dilution of the 1 mM stock with reaction buffer. A suitable range of concentrations based on a complex solution with an absorbance of 0.1 would be 2, 4, 6, 8, 10, 20, 30, 40, 50 and 100 µM; N.B. the final concentrations in the assay will be 50% lower.

The uric acid containing samples (in urine or serum) are diluted with buffer; typical dilutions are 500×, 100× and 10×.

The assay is preferably performed using a multiwell plate reader (the following values assume a 96-well plate is used and that the volume in each well is 200 µL; if a fluorimeter or other plate size is used scalings must be made accordingly).

The calibration is performed by adding 100 µL of each of the uric acid solutions to separate wells on the plate followed by 100 µL of the complex solution; each can be performed in duplicate or triplicate to minimise error. Further wells are then filled with 100 µL of each of the uric acid containing samples to be measured and 100 µL of the complex mixture.

Measurements of emission intensity are performed with a fluorimeter or multi-plate reader fitted with an emission analyser, using excitation in a range suitable for the chromophore and for the case of a combined europium(III) and terbium(III) system at emission wavelengths of 546 (Tb ΔJ=5; 616 (Eu ΔJ=2+Tb ΔJ=3); and 700 nm (Eu ΔJ=4). The inherent differences in sensitivity to quenching of the pair of complexes allows for analysis to be made ratiometrically, each complex effectively acts as an internal reference against which the other is compared.

The calibration curve takes the form of a bi-exponential decay generated by plotting urate concentration against either the 546/616 or 546/700 fluorescence intensity ratios. Determination of the sample urate concentration can then be made by comparison of the appropriate ratio (i.e. 546/616 or 546/700) with the calibration curve, or by fitting the curve mathematically and solving the equation for the ratio.

Values obtained by this method using diluted urine samples from healthy volunteers, (containing varying quantities of ascorbate) were compared to those using a commercial enzymatic kit (Invitrogen, Amplex Red). Each set of data was compared to a standardised solution of sodium urate (assayed by accurate weighing and checked by measuring the absorbance of the solution at 290 nm). For the calibration of the luminescence assay, intensity ratio measurements were made in triplicate for ten different dilutions of a standardised sodium urate solution. Each value recorded was the mean of ten repetitions, using a 96 well plate and an Analytik Flash Scan 530 (excitation at 313 nm). The measured intensity ratio varied by less than 1% in each case.

In analysing samples of urine of unknown uric acid concentration, the urate concentration obtained by the luminescence method was found to be within 10% of the value estimated by the independent enzymatic assay.

Example 5

Quenching by Selected Catechols and Protected Catechols

Catechols constitute a class of electron rich aromatics that also may serve as anti-oxidants. In principle, they are dibasic acids (first $pK_a$ typically around 9.5) with an ene-diol moiety resembling that found in ascorbic acid, and the one electron oxidation potential of catechol itself at pH 7.4 is estimated to be +0.53V (298K). Selected quenching experiments were undertaken comparing the quenching behaviour of the series of catechols 8a-8c (dopamine, DOPA, and the dihydro-cinnamic acid derivative) and the protected catechol, 9 towards [Ln.10] and [Ln.6]$^{3+}$. The synthesis of 10 and similar macrocyclic ligands, and lanthanide (III) complexes thereof, are described in R. A. Poole et al., *Org. Biomol. Chem.*, 2005 (3), 1013-1-24. Quenching data (Table 1), revealed several trends echoing those observed for urate quenching. Europium complexes were quenched less than the Tb analogues, although this effect was less marked for the quenching of [Ln.6]$^{3+}$ by the anionic catechol, 8a. Over narrow quenching ranges, e.g. 0 to 0.1 mM for 8a-8c, and 0 to 1 mM for 9, approximately linear Stern-Volmer plots were obtained. For the case of the cationic complex [Tb.6]$^{3+}$, quenching by dopamine ($K_{sv}^{-1}$=0.17 mM), DOPA ($K_{sv}^{-1}$=0.11 mM) and the cinnamate derivative 8c ($K_{sv}^{-1}$=0.05 mM) followed a trend in accord with the effect of electrostatic repulsion between complex and quencher.

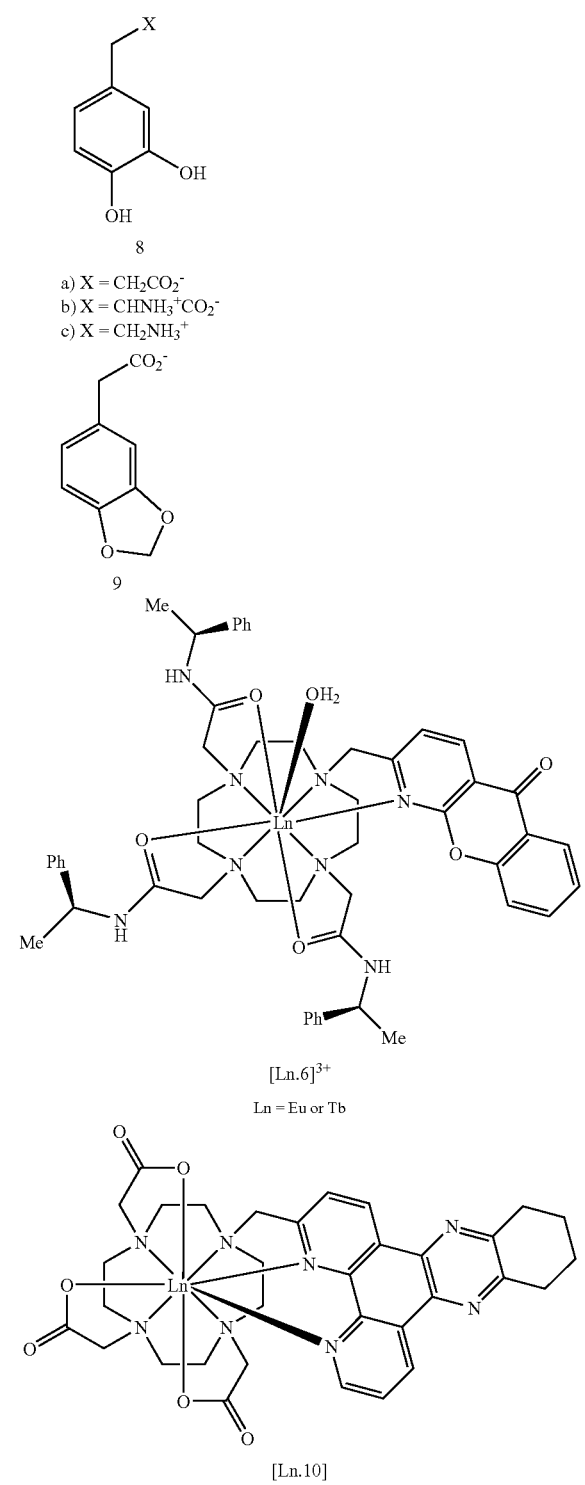

a) X = CH$_2$CO$_2^-$
b) X = CHNH$_3^+$CO$_2^-$
c) X = CH$_2$NH$_3^+$

[Ln.6]$^{3+}$

Ln = Eu or Tb

[Ln.10]

The protected catechol, 9, is much less readily oxidised than 8c in aqueous media, yet still quenched the excited state of [Tb.10](a dpqC derivative) and [Tb.6]$^{3+}$ (an azaxanthone) more readily than iodide $\left(E_{\frac{1}{2}} = +0.54V\right).$ Examination of the cyclic voltammogram of 9 (0.1 M Bu$_4$NPF$_6$, MeCN) revealed an irreversible oxidation wave at +1.50V. The related alcohol (i.e. with CH$_2$CO$_2$H replaced by CH$_2$CH$_2$OH) and the corresponding (deprotected) catechol, 8a, gave oxidation waves at +1.41 and +1.38V respectively.

TABLE 1

Quenching data[a,b] for selected catechols (pH 7.4, 10 mM NaCl, 0.1M, HEPES, 10 μM complex) and for urate, in comparison.

| Complex | 8a | | 9 | | urate | |
|---|---|---|---|---|---|---|
| | $K_{sv}^{-1}$/mM | $\tau_0/\tau$ | $K_{sv}^{-1}$/mM | $\tau_0/\tau$ | $K_{sv}^{-1}$/mM | $\tau_0/\tau$ |
| [Tb.6]$^{3+}$ | 0.05[b] | 3.3[b] | 1.81 | 1.1 | 0.04 | 4.4 |
| [Eu.6]$^{3+}$ | 0.06 | 2.7 | 45 | 1.0 | 0.60 | 1.2 |
| [Tb.10] | 0.06 | 2.4 | 2.0 | 1.04 | 0.006 | 19 |
| [Eu.10] | 0.17 | 1.6 | 15 | 1.01 | 0.11 | 7.5 |

[a]$\tau_0/\tau$ values are reported here at a fixed quencher concentration of 100 μM.
[b]$K_{sv}^{-1}$ ($\tau_0/\tau$ in parenthesis) values for [Tb.6]$^{3+}$ quenching DOPA, 8b, were 0.11 mM ($\tau_0/\tau$ = 2.0) and for dopamine, 8a, corresponding values were $K_{sv}^{-1}$ = 0.17 mM, $\tau_0/\tau$ = 1.6.

The invention claimed is:

1. A method of determining the amount of an analyte having an oxidation potential, for a one electron oxidation process, of about +0.10 to about +1.20 volts at pH 7, relative to the normal hydrogen electrode at 298K, said method comprising measuring the emission intensity or emission lifetime, at two or more wavelengths, from a sample comprising said analyte and two or more different macrocyclic lanthanide (III) complexes, wherein each of said macrocyclic lanthanide (III) complexes comprises a different lanthanide ion but the same macrocyclic ligand, and using a ratio of emission intensities or emission lifetimes measured at two different wavelengths to calculate the amount of analyte in said sample.

2. The method of claim 1 wherein the lanthanide ions in said macrocyclic lanthanide (III) complexes are selected from the group consisting of europium, dysprosium, samarium, terbium, neodymium and ytterbium.

3. The method of claim 1 wherein the lanthanide ions in said macrocyclic lanthanide (III) complexes are selected from the group consisting of europium, dysprosium, samarium and terbium.

4. The method of claim 1 wherein no more than two different macrocyclic lanthanide (III) complexes are present in said sample.

5. The method of claim 4 wherein the lanthanide ions in said two different macrocyclic lanthanide (III) complexes are europium and terbium.

6. The method of claim 1 wherein said macrocyclic ligand comprises a macrocyclic ring attached to a sensitising moiety.

7. The method of claim 6 wherein the ring of said macrocyclic ring comprises 12 atoms.

8. The method of claim 6 wherein said macrocyclic ring is a 1,4,7,10-tetraazacyclododecane.

9. The method of claim 8 where said 1,4,7,10-tetraazacyclododecane is substituted at position 1 with said sensitising moiety and independently at positions 4, 7 and 10 with moieties capable of co-ordinating to the lanthanide ion.

10. The method of claim 6 wherein said sensitising moiety is an azaxanthone, azathioxanthone or tetraazatriphenylene group capable of co-ordinating to the lanthanide ion by a nitrogen atom of an integral pyridyl group; or a derivative of an azaxanthone, azathioxanthone or tetraazatriphenylene in which a nitrogen atom in an integral pyridyl group is replaced with a moiety capable of co-ordinating to the lanthanide ion.

11. The method of claim 10 wherein the moiety is capable of co-ordinating to the lanthanide ion is C—OH or N-oxide.

12. The method of claim 10 wherein said sensitising moiety is an azaxanthone, azathioxanthone or tetraazatriphenylene group.

13. The method of claim 1 wherein the macrocyclic ligand is of formulae 1, 2, 3 or 4:

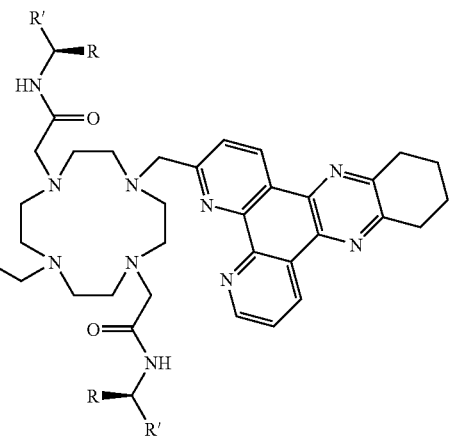

1

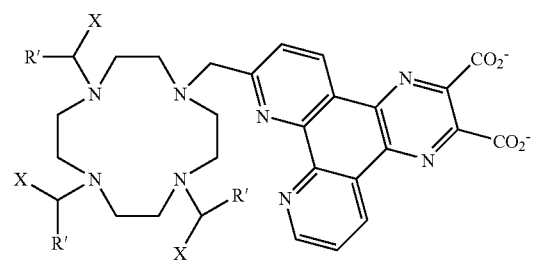

2

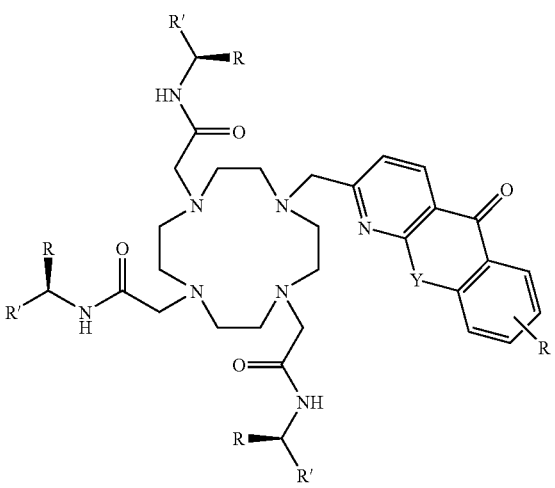

3

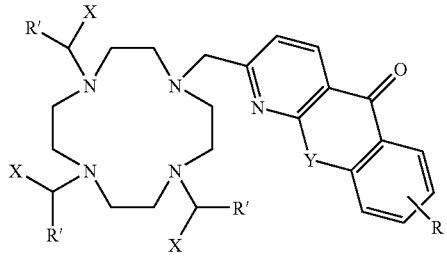

4 wherein

R=H, CO$_2^-$, CO$_2$R', CONHR', NHCOR', C$_{1-6}$ straight-chain, branched, cyclo- or cycloalkyl-alkyl, Ph or CH$_2$Ph;

R'=H, $C_{1-6}$ straight-chain, branched, cyclo- or cycloalkyl-alkyl, Ph, $CH_2Ph$, or $(CH_2)_nCO_2^-$, wherein n=1, 2, 3 or 4;

X=$CO_2^-$, PR"$O_2$ or $PO_2(OR")^{2-}$, wherein R"=H, $C_{1-6}$ straight-chain, branched, cyclo- or cycloalkyl-alkyl, Ph or $CH_2Ph$; and Y=O or S.

14. The method of claim 1 wherein the two or more different macrocyclic lanthanide (III) complexes are of formulae 5, 6 or 7:

5
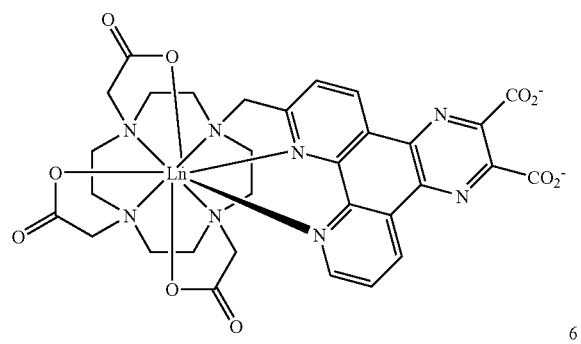

6
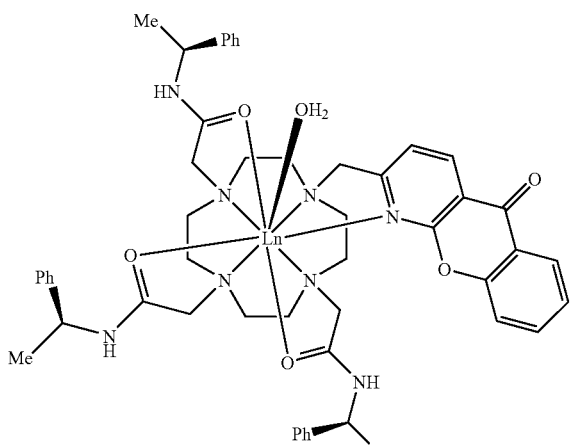

7
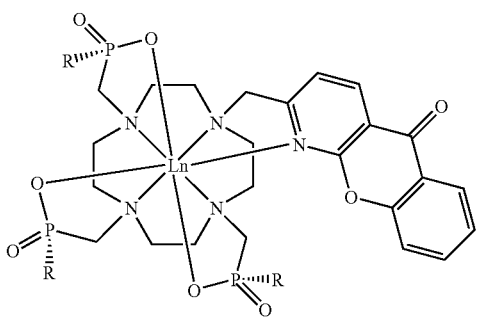

wherein

Ln is the lanthanide (III) ion; and

R is Me or $CH_2Ph$.

15. The method of claim 1 wherein the macrocyclic ligand is of formula 1a:

1a
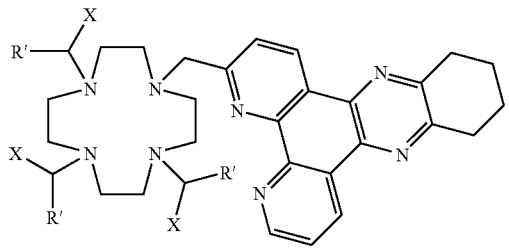

wherein

R'=H, $C_{1-6}$ straight-chain, branched, cyclo- or cycloalkyl-alkyl, Ph, $CH_2Ph$, or $(CH_2)_nCO_2^-$, wherein n=1, 2, 3 or 4; and X=$CO_2^-$, PR"$O_2$ or $PO_2(OR")^{2-}$ wherein R"=H, $C_{1-6}$ straight-chain, branched, cyclo- or cycloalkyl-alkyl, Ph or $CH_2Ph$.

16. The method of claim 15, wherein:

the alkyl of R' is methyl, ethyl, propyl or butyl; and the alkyl of X is methyl, ethyl, propyl or butyl.

17. The method of claim 1 wherein the two or more different macrocyclic lanthanide (III) complexes are of formula 10:

10
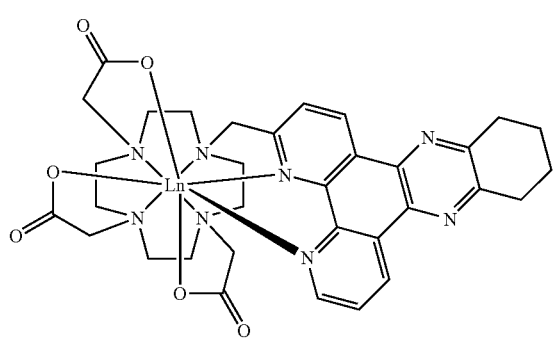

wherein Ln is the lanthanide (III) ion.

18. The method of claim 1 wherein emission intensities are measured.

19. The method of claim 1 wherein the sample comprises a biological fluid.

20. The method of claim 19 wherein the biological fluid is blood, plasma, serum, urine, saliva, mucus, perspiration, lymph, gastric juice, aqueous humor or semen.

21. The method of claim 19 wherein the biological fluid is synovial, amniotic, pericardial, peritoneal, pleural, cerebrospinal, vaginal or faecal.

22. The method of claim 19 wherein the sample comprises urine or serum.

23. The method of claim 19 wherein the fluid is diluted before conducting said method.

24. The method of claim 1 wherein said analyte has an oxidation potential, for a one electron oxidation process, of about +0.25 to about +0.75 volts, at pH 7, relative to the normal hydrogen electrode at 298K.

25. The method of claim 1 wherein said analyte is uric acid, ascorbic acid or a phenolic compound.

26. The method of claim 25 wherein the analyte is a catechol or a catecholamine.

27. The method of claim 25 wherein the analyte is catechin, rutin, quercetin, quinalizarin, ellagic acid, umbelliferone, esculetin, caffeic acid, dihydroxyphenyl-alanine (DOPA), norepinephrine, 5-hydroxytryptophan, or serotonin.

28. The method of claim 25 wherein said analyte is uric acid.

* * * * *